(12) United States Patent
Park et al.

(10) Patent No.: US 12,188,027 B2
(45) Date of Patent: Jan. 7, 2025

(54) **SURFACE EXPRESSION VECTOR USING TWO KINDS OF PROMOTERS DERIVED FROM *LACTOBACILLUS CASEI* FOR CONCURRENTLY EXPRESSING TWO TARGET PROTEINS AND METHOD FOR EXPRESSING PROTEINS ON MICROBIAL SURFACE BY USING SAME**

(71) Applicant: BIOLEADERS CORPORATION, Yongin-si (KR)

(72) Inventors: Young Chul Park, Seoul (KR); Dae Eun Ki, Seoul (KR); Gyeong Jun Nam, Yongin-si (KR); Se Eun Byeon, Hwaseong-si (KR); Ha Na Moon, Yongin-si (KR); Hyun Jun Kang, Goyang-si (KR); Kyung Soo Hahm, Seoul (KR)

(73) Assignee: BIOLEADERS CORPORATION, Yongin-si (KR)

( * ) Notice: Subject to any disclaimer, the term of this patent is extended or adjusted under 35 U.S.C. 154(b) by 857 days.

(21) Appl. No.: 17/281,756

(22) PCT Filed: Oct. 10, 2019

(86) PCT No.: PCT/KR2019/013261
§ 371 (c)(1),
(2) Date: Mar. 31, 2021

(87) PCT Pub. No.: WO2020/076079
PCT Pub. Date: Apr. 16, 2020

(65) Prior Publication Data
US 2023/0295644 A1 Sep. 21, 2023

(30) Foreign Application Priority Data
Oct. 10, 2018 (KR) .................. 10-2018-0120547

(51) Int. Cl.
*C12N 15/74* (2006.01)
*C12N 9/88* (2006.01)
*C12N 15/62* (2006.01)

(52) U.S. Cl.
CPC ............. *C12N 15/746* (2013.01); *C12N 9/88* (2013.01); *C12N 15/62* (2013.01); *C07K 2319/035* (2013.01); *C12Y 401/02013* (2013.01)

(58) Field of Classification Search
CPC ........ C12N 15/746; C12N 9/88; C12N 15/62; C07K 2319/035; C12Y 401/02013
See application file for complete search history.

(56) References Cited

U.S. PATENT DOCUMENTS

| 7,553,636 B2 * | 6/2009 | Sung ............. C12Y 207/08005 435/69.7 |
| 8,236,940 B2 * | 8/2012 | Sung ................... C12N 15/746 435/71.1 |
| 2004/0253704 A1 * | 12/2004 | Sung ................... C12N 9/1051 435/221 |
| 2011/0091493 A1 | 4/2011 | Moahamadzadeh et al. |

FOREIGN PATENT DOCUMENTS

| CN | 101426919 A | 5/2009 | |
| JP | 2001514518 | 9/2001 | |
| JP | 2010088332 | 4/2010 | |
| JP | 2012514469 | 6/2012 | |
| KR | 20040034780 | 4/2004 | |
| KR | 20080086161 | 9/2008 | |
| WO | 2003014360 | 2/2003 | |
| WO | 2008115019 | 9/2008 | |
| WO | WO-2008115019 A1 * | 9/2008 | ................ A61P 1/04 |

OTHER PUBLICATIONS

Sasaki, S., Takeshita, F., Oikawa, T., Kojima, Y., Xin, K. Q., Okuda, K., & Ishii, N. (2004). Improvement of DNA vaccine immunogenicity by a dual antigen expression system. Biochemical and biophysical research communications, 315(1), 38-43. (Year: 2004).*
Bettenbrock, Katja, and Carl-Alfred Alpert. "The gal genes for the Leloir pathway of *Lactobacillus casei* 64H." Applied and environmental microbiology 64.6 (1998): 2013-2019. (Year: 1998).*
Öztürk, Sibel, Burcu Gündüz Ergün, and Pinar çalk. "Double promoter expression systems for recombinant protein production by industrial microorganisms." Applied Microbiology and Biotechnology 101 (2017): 7459-7475. (Year: 2017).*
Vemanna, et al., A Modified MultiSite Gateway Cloning Strategy for Consolidation of Genes in Plants, Mol Biotechnol, 2012.
Georgiou, et al., Practical applications of engineering Gram-negative bacterial cell surfaces, Tibtech, Jan. 1993, vol. 11, pp. 6-10.
International Search report—PCT/KR2019/013261 dated Aug. 27, 2020.
Lee, et al., Microbial cell-surface display, Trends in Biotechnology, vol. 21, No. 1, Jan. 2003, pp. 45-52.
(Continued)

*Primary Examiner* — Tracy Vivlemore
*Assistant Examiner* — Allison Marie Johnson
(74) *Attorney, Agent, or Firm* — CANTOR COLBURN LLP

(57) ABSTRACT

Provided is a vector capable of co-expressing two different target proteins on the microbial surface using two promoters derived from *Lactobacillus*, and a method of expressing target proteins on the microbial surface using the vector. The vector containing foreign genes inserted therein is transformed into a microorganism, and allows different foreign proteins to be stably expressed on the surface of the microorganism. Furthermore, provided is a surface expression vector containing the gene pgsA encoding a poly-gamma-glutamate synthetase complex, and a method of expressing a target protein on the microbial surface using the vector. The vector containing foreign genes inserted therein is transformed into a microorganism, and allows the foreign proteins to be stably expressed on the surface of the microorganism.

11 Claims, 14 Drawing Sheets
Specification includes a Sequence Listing.

(56) References Cited

OTHER PUBLICATIONS

NCBI. GenBank accession No. FM177140.1. *Lactobacillus casei* BL23 complete genome, strain BL23 (Feb. 27, 2015).

Sasaki, et al., Improvement of DNA vaccine immunogenicity by a dual antigen expression system, Biochemical and Biophysical Research Communications, 2004, vol. 315, pp. 38-43.

Kim et al., Two-promoter vector is highly efficient for overproduction of protein complexes, Protein Science, 2004, vol. 13, pp. 1698-1703, Cold Spring Harbor Laboratory Press.

Berlec, et al., Single plasmid systems for inducible dual protein expression and for CRISPR-Cas9/CRISPRi gene regulation in lactic acid bacterium *Lactococcus lactis*, Scientific Reports, 2018, vol. 8.

Mao, et al., Surface display on lactic acid bacteria without genetic modification: strategies and applications, Applied Microbiology and Biotechnology, 2016, vol. 100, pp. 9407-9421.

Chinese Notice of Allowance—Chinese Application No. 201980076721.1 dated Aug. 12, 2024.

\* cited by examiner

SURFACE EXPRESSION VECTOR USING TWO KINDS OF PROMOTERS DERIVED FROM *LACTOBACILLUS CASEI* FOR CONCURRENTLY EXPRESSING TWO TARGET PROTEINS AND METHOD FOR EXPRESSING PROTEINS ON MICROBIAL SURFACE BY USING SAME

TECHNICAL FIELD

The present invention relates to a vector which co-expresses two different genes on the microbial surface using an aldolase promoter and galactose mutarotase promoter derived from *Lactobacillus casei*, and a microorganism transformed with this vector.

In addition, the present invention relates to a novel vector, which effectively expresses a foreign protein on the microbial surface using an outer membrane protein (pgsA) which is derived from a *Bacillus* sp. strain and involved in the synthesis of poly-gamma-glutamate. Furthermore, the present invention relates to a method of producing a protein by expressing a foreign protein on the microbial surface using an outer membrane protein which is derived from a *Bacillus* sp. strain and involved in the synthesis of poly-gamma-glutamate.

BACKGROUND ART

Cell surface display or cell surface expression refers to a technique by which a protein or a peptide is fused with an appropriate surface anchoring motif and expressed on the surface of Gram-negative or Gram-positive bacteria, fungus, yeast, or animal cells (Lee S. Y., et al., Trends Biotechnol., 21:4552, 2003). The first cell surface display technique was developed in 1980s using phage having a relatively simple surface, and is a technique in which a peptide or a small protein is fused with pIII of filamentous phage and expressed. Thus, the first cell surface display technique was named the surface-expression system. Cell surface display using phage has been used for screening of antibodies, epitopes, and high-affinity ligands, but has a limitation in that the size of protein that can be displayed on the phage surface is relatively limited. Thus, as an alternative thereto, cell surface expression using bacteria has been developed. This cell surface display is a technique in which a foreign protein is stably expressed on the microbial surface by using a surface protein of a microorganism such as bacteria or yeast as a surface anchoring motif.

In order to express a foreign protein on the cell surface using an outer membrane protein of a specific organism, a suitable surface protein and the foreign protein should be linked with each other at the gene level to form a fusion protein, and the fusion protein should stably pass through the inner cell membrane and should be attached to and maintained on the cell surface. To this end, a protein having the following properties is preferably used as the surface anchoring motif. Namely, (1) the protein has, at the N-terminus, a secretion signal capable of passing through the inner cell membrane; (2) the protein should have a targeting signal which can be stably attached onto the outer cell membrane; (3) the protein can be expressed on the cell surface in large amounts within the range that does not adversely affect the growth of cells, so that the protein can show high activity; and (4) the protein should be able to be stably expressed regardless of the size thereof such that it can be used in various reactions (Georgiou et al., TIBTECH, 11:6, 1993). In addition, this surface anchoring motif also needs to be genetically engineered such that it is inserted into the N-terminus, C-terminus or central portion of the outer membrane protein on the surface of a host cell (Lee et al., TIBTECH, 21:45-52, 2003).

In order for a protein to be expressed on the bacterial surface, the protein should have, in the primary sequence thereof, a secretion signal enabling the protein biosynthesized in the cell to pass through the cell membrane. In addition, in the case of Gram-negative bacteria, the protein should pass through the inner cell membrane and the cell membrane space, should be inserted into and attached to the outer cell membrane, and should be anchored to the membrane so as to protrude outward from the membrane.

In the case of bacteria, examples of proteins that have this secretion signal and a targeting signal for protein anchoring to the cell surface include surface proteins, special enzymes, and toxin proteins. In fact, if the secretion signals and target signals of these proteins are used together with proper promoters, the proteins can be successfully expressed on the bacterial surface.

Meanwhile, attempts to produce useful foreign proteins in lactic acid bacteria have been mainly made by using an inducible promoter as an inducer or by ensuring a highly efficient promoter. Although the development of various applications of and academic studies on lactic acid bacteria expressing target proteins as described above have been actively conducted, there are still problems in that the expression levels of the target proteins are insufficient, and in that, when a protein obtained using an inducible expression promoter is administered in vivo, sustained expression of the protein may not be possible.

In recent years, in the United States and Europe, studies have been conducted on the development of live vaccines using lactic acid bacteria, and on carriers for delivering useful hormone drugs into the intestines and the establishment of efficient genetic resources therefor, and on the development of insertion vectors for lactic acid bacteria. In particular, since unmethylated CpG DNA, lipoteichoic acid, peptidoglycan and the like, which are contained in large amounts in lactic acid bacteria, are known to act as immune adjuvants, lactic acid bacteria have been considered highly useful as vaccine vehicles. In addition, lactic acid bacteria have a number of advantages in that they can deliver antigens to the intestines due to their resistance to bile acid and gastric acid, and thus induce mucosal immunity in the intestines.

However, in order to use lactic acid bacteria as vaccine vehicles, it is necessary to develop a technology of facilitating antigen-antibody reactions by presenting antigen proteins for production of disease-preventing antibodies to the inside or outside of cells.

Meanwhile, galactose mutarotase is known to play an important role in normal galactose metabolism by catalyzing the conversion of β-D-galactose to α-D-galactose in the Leloir pathway which is a metabolic pathway for D-galactose catabolism. However, studies on the molecular biological characteristics of this galactose mutarotase in lactic bacteria are still insufficient.

Accordingly, the present inventors have developed a surface expression vector which effectively expresses two different foreign proteins on the microbial surface using a strain which expresses the HPV E7 protein on the cell surface thereof, and a method for stably expressing large amounts of two different foreign proteins on the microbial surface. Furthermore, the present inventors have conducted extensive studies on the use of a gene (pgsA), which is involved in the synthesis of poly-gamma-glutamate, as a novel surface anchoring motif, and as a result, have developed a novel vector which is effectively expresses foreign proteins on the microbial surface using the pgsA gene, and a method for expressing large amounts of foreign proteins on the microbial surface, thereby completing the present invention.

DISCLOSURE

Technical Problem

The present invention is intended to provide a surface expression vector which co-expresses two target proteins on the microbial surface using a poly-gamma-glutamate synthetase complex gene, derived from a *Bacillus subtilis* var. Chungkookjang strain, as a surface anchoring motif capable of expressing large amounts of two foreign proteins on the microbial surface, and using an aldolase promoter and galactose mutarotase promoter derived from *Lactobacillus casei*, and a method of efficiently expressing two different foreign proteins on the surface of a transformant obtained by transformation with the surface expression vector.

The present invention is also intended to provide a method including: selecting an outer membrane protein, which is derived from a *Bacillus* sp. strain and involved in the synthesis of poly-gamma-glutamate, as a surface anchoring motif capable of expressing a large amount of a foreign protein on the microbial surface; constructing a surface expression vector capable of expressing a foreign protein or peptide on the microbial surface using the selected outer membrane protein; and efficiently expressing a foreign protein on the surface of a transformant obtained by transformation with the surface expression vector.

Technical Solution

To achieve the above objects, the present invention provides a surface expression vector for expressing target proteins, the surface expression vector including: a first promoter, a gene encoding a poly-gamma-glutamate synthetase complex for surface anchoring, and a gene encoding the target protein; and a second promoter, a gene encoding a poly-gamma-glutamate synthetase complex for surface anchoring, and a gene encoding a target protein.

In the present invention, the first promoter may be represented by SEQ ID NO: 1.

In the present invention, the second promoter may be represented by SEQ ID NO: 2.

In the present invention, the gene encoding the poly-gamma-glutamate synthetase complex may be derived from a *Bacillus* sp. strain that produces the gamma-glutamate synthetase complex.

In the present invention, a linker may be inserted into an end of the gene encoding the poly-gamma-glutamate synthetase complex, and the gene encoding the target protein may be inserted into the inserted linker.

In the present invention, the target protein may be one in which a portion of the amino acid sequence of the target protein has been removed or mutated in a site-directed manner so as to favor surface expression.

In the present invention, the first promoter may be an aldolase promoter (Pald) derived from lactic acid bacteria.

In the present invention, the second promoter may be a galactose mutarotase promoter (Pgm) derived from lactic acid bacteria.

In the present invention, the vector may be applied to Gram-negative or Gram-positive bacteria.

The present invention also provides a microorganism transformed with the surface expression vector. In the present invention, a microorganism used for the transformation may be a microorganism modified so that it does not produce an intracellular or extracellular protease, which is involved in degradation of the expressed target protein, in order to favor cell surface expression of the target protein.

In the present invention, the microorganism that is used as a host may be lactic acid bacteria. In the present invention, examples of the lactic acid bacteria include *Lactobacillus* sp., *Streptococcus* sp., and *Bifidobacterium* sp. Typically, as the host, the *Lactobacillus* sp. may be selected from among *L. acidophilus, L. casei, L. plantarum, L. ferementum, L. delbrueckii, L. johnsonii* LJI, *L. reuteri*, and *L. bulgaricus*; the *Streptococcus* sp. may be *S. thermophilus*; and the *Bifidobacterium* sp. may be selected from among *B. infantis, B. bifidum, B. longum, B. psuedolongum, B. breve, B. lactis* Bb-12, and *B. adolescentis*. More preferably, the microorganism is *Lactobacillus* sp.

The present invention also provides a method for cell surface expression of a target protein, the method including steps of: expressing the target protein on the cell surface by culturing the transformed microorganism; and recovering cells having the target protein expressed on the surface thereof.

In the present invention, the target protein may be any one selected from the group consisting of hormones, hormone analogs, enzymes, enzyme inhibitors, signaling proteins or fragments thereof, antibodies or fragments thereof, single chain antibodies, binding proteins, binding domains, peptides, antigens, adhesion proteins, structural proteins, regulatory proteins, toxin proteins, cytokines, transcription regulatory factors, coagulation factors, and plant biodefense-inducing proteins.

The present invention also provides a method of expressing a target protein on the surface of a Gram-negative or Gram-positive cell, the method including steps of: (a) constructing a recombinant vector by inserting a protein encoding the target protein into the surface expression vector; (b) transforming a Gram-negative or Gram-positive host cell with the recombinant vector; and (c) expressing the target protein on the surface of the transformed host cell by culturing the transformed host cell.

The present invention also provides a surface expression vector for expressing a target protein, the surface expression vector including: a gene pgsA encoding a poly-gamma-glutamate synthetase complex; and a gene encoding the target protein.

In the present invention, the pgsA may be derived from a *Bacillus* sp. strain that produces poly-gamma-glutamate.

In the present invention, the gene pgsA encoding the poly-gamma-glutamate synthetase complex may have the nucleotide sequence of any one of SEQ ID NOs: 21 to 25 and 32 to 34. Preferably, the gene pgsA encoding the poly-gamma-glutamate synthetase complex may have the nucleotide sequence of any one of SEQ ID NOs: 21 to 24 and 32 to 34.

In the present invention, a linker may be inserted into an end of the gene encoding the poly-gamma-glutamate synthetase complex, and the gene encoding the target protein may be inserted into the inserted linker.

In the present invention, the target protein may be one in which a portion of the amino acid sequence of the target protein has been removed or mutated in a site-directed manner so as to favor surface expression.

In the present invention, the promoter may be an aldolase promote derived from lactic acid bacteria.

The present invention also provides a microorganism transformed with the surface expression vector. In the present invention, the microorganism used for the transformation may be a microorganism modified so that it does not produce an intracellular or extracellular protease, which is involved in degradation of the expressed target protein, in order to favor cell surface expression of the target protein.

The present invention also provides a method for cell surface expression of a target protein, the method including steps of: expressing the target protein on the cell surface by culturing the transformed microorganism; and recovering cells having the target protein expressed on the surface thereof.

In the present invention, the target protein may be any one selected from the group consisting of hormones, hormone analogs, enzymes, enzyme inhibitors, signaling proteins or fragments thereof, antibodies or fragments thereof, single chain antibodies, binding proteins, binding domains, peptides, antigens, adhesion proteins, structural proteins, regulatory proteins, toxin proteins, cytokines, transcription regulatory factors, coagulation factors, and plant biodefense-inducing proteins.

The present invention also provides a method of inducing humoral immunity or cellular immunity by administering cells, produced by the above-described method and having an antigen expressed on the surface thereof, to vertebrates other than humans.

The present invention also provides a method of producing an antibody in vertebrates other than humans, the method including: inducing an immune response by administering cells, produced by the above-described method and having an antigen expressed on the surface thereof, to the vertebrates; and recovering an antibody produced by the immune response.

The present invention also provides a surface expression vector for expressing a target protein, wherein the vector is applied to Gram-negative or Gram-positive bacteria.

The present invention also provides a method of expressing a target protein on the surface of a Gram-negative or Gram-positive host cell, the method including steps of: (a) constructing a recombinant vector by inserting a gene encoding the target protein into the surface expression vector; (b) transforming the Gram-negative or Gram-positive host cell with the recombinant vector; and (c) expressing the target protein on the surface of the transformed host cell by culturing the transformed host cell.

Advantageous Effects

The surface expression vector according to the present invention is a single vector including: two different promotes; genes encoding a poly-gamma-glutamate synthetase complex for surface anchoring; and target protein-encoding genes linked to the genes encoding the poly-gamma-glutamate synthetase complex, respectively. Thus, the surface expression vector according to the present invention has advantages over prior art inventions in that it may co-express two different target proteins, and the possibility of cellular transformation that may occur in two transformation processes may be minimized because a microorganism transformed with the surface expression vector is used. In addition, since the surface expression vector is a single vector containing two different promoters, it may efficiently express target proteins within a shorter time than conventional art inventions, and has an excellent effect of remarkably reducing drug development costs by selecting substances with high drug potential rapidly and expressing two different target proteins by the single surface expression vector. Moreover, the surface expression vector for expressing target proteins according to the present invention may stably express target proteins. In addition, the surface expression vector according to the present invention may constitutively express target proteins on the surface of a recombinant microorganism. Thus, the surface expression vector may be advantageously used in the production of antigens for the manufacture of vaccines required.

BEST MODE

Example 1: Construction of Surface Expression Vector pKV-Pald-pgsA-HPV16E7_Pgm-pgsA-EGFP for Co-Expression of Two Antigens To construct a surface expression vector for co-expression of two antigens, using the surface expression vector pKV-Pald-pgsA-E7 (pKV-Pald-pgsA380L-HPV16E7; see Korean Patent No. 10-1471043), a gene encoding Pgm-pgsA-EGFP was inserted into the C-terminus of Pald-pgsA-HPV16E7 to obtain the vector pKV-Pald-pgsA-HPV16E7_Pgm-pgsA-EGFP capable of co-expressing two different target proteins on the surface of lactic acid bacteria.

First, to construct an EGFP expression vector, the HPV16 E7 gene fused with pgsA pKV-Pald-PgsA-E7 (see Korean Patent No. 10-1471043) was removed, and a gene encoding EGFP was inserted into the vector.

Using the synthesized EGFP gene fragment, PCR was using the primers of SEQ ID NO: 3 and SEQ ID NO: 4.

```
SEQ ID NO 3:
5'-TGGTGGATCCGTGAGCAAGGGCGAGGAGCTG-3'

SEQ ID NO 4:
5'-TGACTCTAGAACTAGTGTCGACGGTACCTTACTTGTACAGCTCGTC
C-3'
```

As a result, a 755-bp EGFP gene fragment was obtained, which contains a BamHI restriction enzyme site at the 5' end thereof and an XbaI restriction enzyme site at the 3' end thereof. The obtained DNA fragment was treated with BamHI and XbaI restriction enzymes, the vector pKV-Pald-pgsA-E7 was cleaved with BamHI and XbaI to remove the HPV16 E7 gene region, and then the EGFP gene and the cleaved vector were ligated to each other to obtain pKV-Pald-pgsA-EGFP.

In addition, in order to replace the aldolase promoter in the pKV-Pald-pgsA-EGFP vector by a galactose mutarotase promoter, the *Lactobacillus casei* genome was subjected to PCR using the primers of SEQ ID NO: 5 and SEQ ID NO: 6 to obtain a galactose mutarotase promoter fragment containing an SphI restriction enzyme site at the 5' end thereof and a XbaI restriction enzyme site at the 3' end thereof. The obtained DNA fragment was treated with SphI and XbaI restriction enzymes, and the vector pKV-Pald-pgsA-EGFP was also cleaved with the same restriction enzymes to remove the aldolase promoter region, and then the galactose mutarotase promoter and the cleaved promoter were ligated to each other to obtain pKV-Pgm-pgsA-EGFP.

```
SEQ ID NO 5:
5'-TACGGCATGCTTGAATTGGTTTCTTACGAT-3'

SEQ ID NO 6:
5'-TACGCTCGAGGTTGAATTACCTCCTAATAG-3'
```

Finally, in order to insert Pgm-pgsA-EGFP into the C-terminus of the E7 region of the pKV-Pald-pgsA-E7 vector, PCR was performed using the pKV-Pgm-pgsA-EGFP vector as a template and the primers of SEQ ID NO: 7 and SEQ ID NO: 8.

```
SEQ ID NO 7:
5'-GCGCGAATTCTTGAATTGGTTTCTTACGA-3'

SEQ ID NO 8:
5'-GCGCTGCGCATTACTTGTACAGCTCGTC-3'
```

Figure 1:
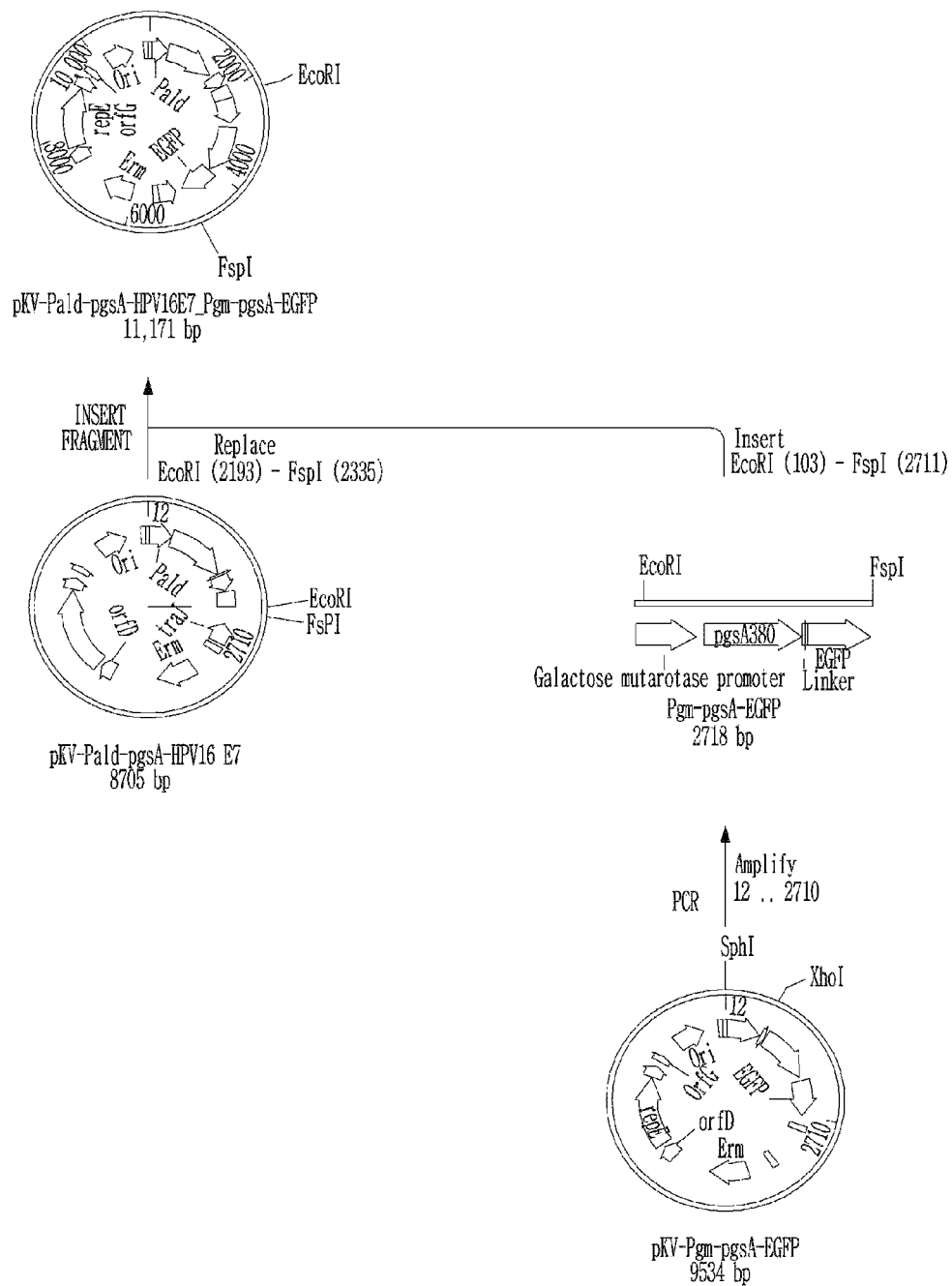
FIG. 1 shows a method of constructing a surface expression vector capable of expressing two target proteins on the microbial surface.
Figure 2:
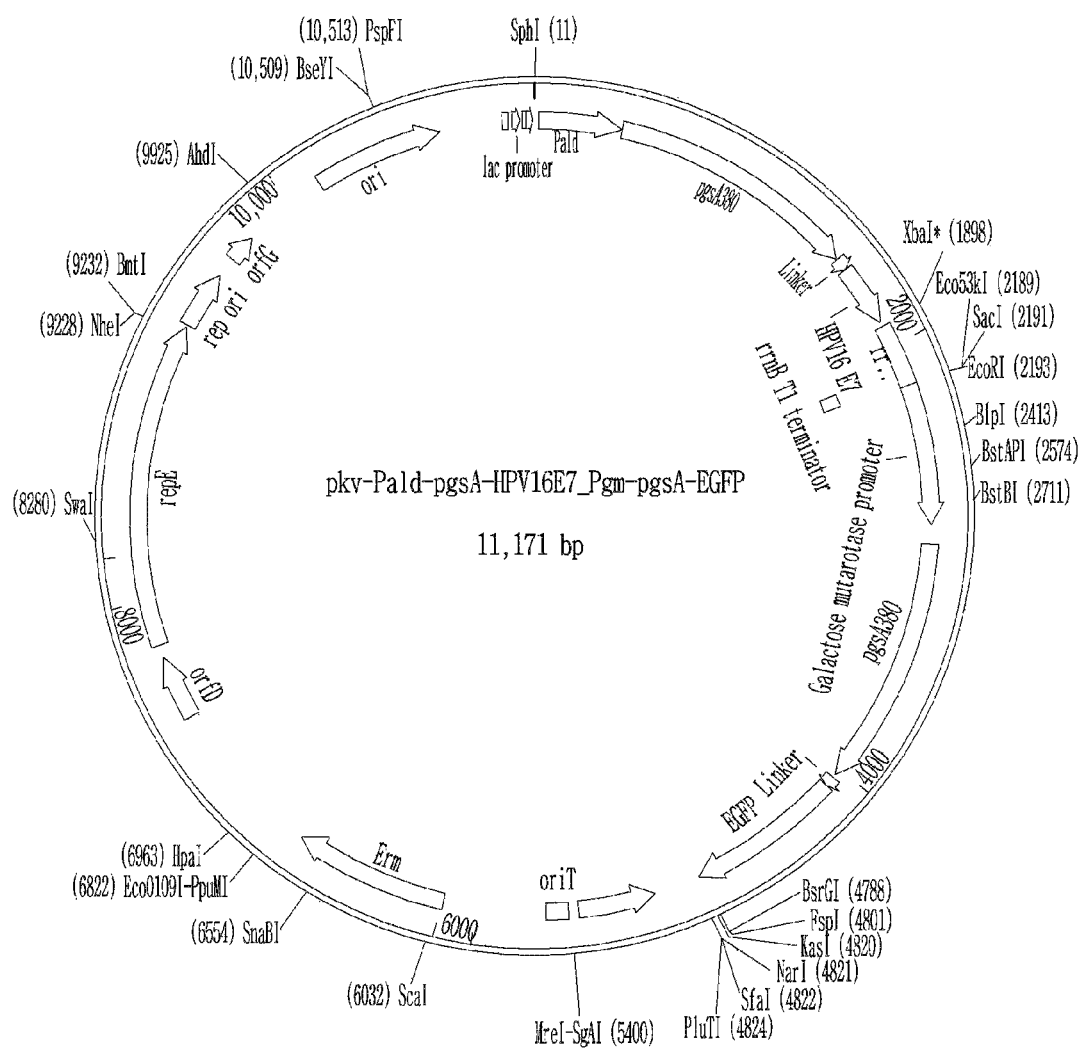
FIG. 2 shows a genetic map of the surface expression vector pKV-Pald-pgsA-HPV16E7_Pgm-pgsA-EGFP according to the present invention.

As a result, a 2608-bp fragment including the Pgm-pgsA-EGFP gene was obtained, which contains an EcoRI restriction enzyme site at the 5' end thereof and an FspI restriction enzyme site at the 3' end thereof. The obtained DNA fragment, which is a gene encoding Pgm-pgsA-EGFP, was inserted into the surface expression vector pKV-Pald-pgsA-HPV16E7 using the EcoRI and FspI restriction enzyme sites to obtain pKV-Pald-pgsA-HPV16E7 Pgm-pgsA-EGFP which is a 1,1171-bp fragment (FIGS. 1 and 2).

MODE FOR INVENTION

The present invention provides a surface expression vector which co-expresses two target proteins on the microbial surface using a poly-gamma-glutamate synthetase complex gene, derived from a *Bacillus subtilis* var. Chungkookjang strain, as a surface anchoring motif capable of expressing large amounts of two foreign proteins on the microbial surface, and using an aldolase promoter and galactose mutarotase promoter derived from *Lactobacillus casei*, and a method of efficiently expressing two different foreign proteins on the surface of a transformant obtained by transformation with the surface expression vector.

Hereinafter, the present invention will be described in more detail.

The present invention provides a surface expression vector for expressing target proteins, the surface expression vector including: the surface expression vector including: a first promoter, a gene encoding a poly-gamma-glutamate synthetase complex for surface anchoring, and a gene encoding the target protein; and a second promoter, a gene encoding a poly-gamma-glutamate synthetase complex for surface anchoring, and a gene encoding a target protein In the present invention, the term "promoter" refers to a minimal sequence sufficient to direct transcription.

The aldolase promoter and galactose mutarotase promoter of the present invention are promoters that induce expression of aldolase gene and galactose mutarotase gene, respectively, in *Lactobacillus casei*. In general, a promoter contains a region to which RNA polymerase binds to induce the initiation of transcription, and the degree of RNA synthesis is determined depending on the nucleotide sequence of the promoter. Thus, the expression level of a gene may vary depending on the type of promoter. In the present invention, in order to obtain the aldolase promoter and the galactose mutarotase promoter, the *Lactobacillus casei* genome was amplified by PCR, and a 406-bp promoter (SEQ ID NO: 1) and 607-bp promoter (SEQ ID NO: 2) derived from *Lactobacillus casei* were isolated using gene cloning technology.

In the present invention, the term "vector" refers to a gene construct including a nucleotide sequence of a gene operably linked to suitable regulatory sequences so as to be capable of expressing a target gene in a suitable host. The regulatory sequences may include a promoter capable of initiating transcription, any operator sequence for regulating such transcription, and sequences that regulate termination of transcription and translation.

The vector of the present invention is not particularly limited as long as it is capable of replicating in cells, and any vector known in the art may be used in the present invention. For example, the vector may be a plasmid, cosmid, phage particle, or viral vector. The vector may further include an additional promoter, etc. Specifically, the vector may further include any element that can help in the surface expression of the target protein without interfering with the operation of the following components: a first promoter, a gene encoding a poly-gamma-glutamate synthetase complex for surface anchoring, and a gene encoding the target protein; and a second promoter, a gene encoding a poly-gamma-glutamate synthetase complex for surface anchoring, and a gene encoding a target protein.

In the present invention, when a gene encoding the target protein to be expressed is operably to the surface expression vector, the surface expression vector may be used as a target-protein expression vector capable of expressing the target protein with high efficiency. The surface expression vector may expression the target protein in a host cell.

In the present invention, the term "operably linked" means that a nucleic acid expression control sequence and a nucleic acid sequence encoding a target protein are functionally linked to each other so as to perform a general function. For example, a promoter and a nucleic acid sequence encoding a protein or RNA can be operably linked to each other so as to affect expression of the coding sequence. The operable linkage to the surface expression vector may be prepared using a gene recombinant technique well known in the art, and site-specific DNA cleavage and linkage may be performed using an enzyme commonly known in the art.

In the present invention, the first promoter may be represented by SEQ ID NO: 1, but is not limited thereto.

In the present invention, the second promoter may be represented by SEQ ID NO: 2, but is not limited thereto.

A variant of the nucleotide sequence represented by SEQ ID NO: 1 or 2 are also included within the scope of the present invention. In the present invention, the first promoter aldolase promoter nucleic acid molecule and the second promoter galactose mutarotase promoter nucleic acid molecule are meant to include functional equivalents of the nucleic acid molecules, for example, variants which result from deletion, substitution or insertion of a portion of the nucleotide sequence of each of the first promoter aldolase promoter and the second promoter galactose mutarotase promoter, but are capable of having the same function as the first promoter aldolase promoter and second promoter galactose mutarotase promoter nucleic acid molecules. Specifically, each of the first promoter aldolase promoter and the second promoter galactose mutarotase promoter may comprise a nucleotide sequence having a sequence homology of at least 70%, more preferably at least 80%, even more preferably at least 90%, most preferably at least 95%, to the nucleotide sequence of SEQ ID NO: 1 or 2. "% of sequence homology" to polynucleotides is identified by comparing two optimally aligned sequences by the comparison region, and a portion of the polynucleotide sequence in the comparison region may include addition or deletion (i.e., gap) compared to the reference sequence (without addition or deletion) for the optimal alignment of the two sequences.

In the present invention, the first promoter, the gene encoding the poly-gamma-glutamate synthetase complex for surface anchoring, and the gene encoding the target protein; and the second promoter, the gene encoding the poly-gamma-glutamate synthetase complex for surface anchoring, and the gene encoding a target protein are arranged consecutively, so that the expressions of the target proteins by the two different promoters located in the "single promoter" are driven independently of each other. Since the promoters that operate independently of each other are present in the single vector, it is possible to more efficiently express the target proteins on the cell surface by effectively reducing the number of surface expression vector construction steps compared to prior art inventions. In addition, the present invention has an advantage in that, since the two different promoters are present in the single vector, it is possible to minimize the possibility of cellular transformation that may occur in two transformation processes that are performed to express two target proteins on the cell surface in a conventional art. In addition, the cell surface expression according to the present invention has an advantage in that the expressions of two genes are driven independently of each other by the respective promoters, so that the expressions of the different target proteins can be independently confirmed.

In another aspect, the present invention provides a microorganism transformed with the surface expression vector. Preferably, the microorganism may be lactic acid bacteria, more preferably probiotic Gram-positive lactic acid bacteria. Common selection criteria for probiotic microorganisms include the following: (i) a microorganism derived from humans; (i) stability against bile, acid, enzyme and oxygen; (i ability to adhere to intestinal mucosa; (iv) colonization potential in the human gastrointestinal tract; (v) production of antimicrobial substances; and (vi) demonstrable efficacy and safety. On the basis of such criteria, it is apparent that lactic acid bacteria are biocompatible and harmless to the human body. Thus, when transformants which use lactic acid bacteria as a host are applied to the human body in order to deliver a gene or protein for preventing or treating disease, a step of detoxifying bacterial strains is not required, unlike a conventional method of producing vaccines using bacterial strains.

In the present invention, examples of the lactic acid bacteria include *Lactobacillus* sp., *Streptococcus* sp., and *Bifidobacterium* sp. Typically, as the host, the *Lactobacillus* sp. may be selected from among *L. acidophilus, L. casei, L. plantarum, L. feremenrum, L. delbrueckii, L. johnsonii* LJI, *L. reuteri*, and *L. bulgaricus*; the *Streptococcus* sp. may be *S. thermophilus*; and the *Bifidobacterium* sp. may be selected from among *B. infantis, B. bifidum, B. longum, B. psuedolongum, B. breve, B. lactis* Bb-12, and *B. adolescentis*. More preferably, the lactic acid bacteria is *Lactobacillus* sp.

In addition, the microorganism used for the transformation may include a transformed microorganism modified so that it does not produce an intracellular or extracellular protease, which is involved in degradation of the expressed target protein, in order to favor cell surface expression of the target protein.

In another aspect, the present invention provides a method for cell surface expression of a target protein, the method including steps of: expressing the target protein on the cell surface by culturing a microorganism transformed with the surface expression vector; and recovering cells having the target protein expressed on the surface thereof. In particular, the present invention provides a method for producing a foreign target protein, which allows the target protein to be efficiently used without a cell disruption or protein isolation/purification process by expressing the foreign target protein on the microbial surface using the surface expression vector of the present invention.

In the present invention, the term "target protein" or "foreign protein" refers to a protein that cannot normally exist in a transformed host cell expressing the protein. For example, when a virus-derived or tumor-derived protein is manipulated to be artificial expressed in lactic acid bacteria, the protein will be referred to as "foreign protein" or "target protein".

Preferably, examples of the target protein include, but are not limited to, infectious microorganisms, immune disease-derived antigens or tumor-derived antigens, for example, fungal pathogens, bacteria, parasites, helminths, viruses or allergy-causing substances. More preferably, examples of the antigen include tetanus toxoid, influenza virus hemagglutinin or nuclear protein, diphtheria toxoid, HIV gp120 or fragments thereof, HIV gag protein, IgA protease, insulin peptide B, *Spongospora subterranea* antigen, *Vibriose* antigen, *Salmonella* antigen, *Pneumococcus* antigen, RSV (respiratory syncytial virus) antigen, *Hemophilus influenza* outer membrane protein, *Streptococcus pneumoniae* antigen, *Helicobacter pylori* urease, *Neisseria meningitidis* pilin, *N. gonorrhoeae* pilin, melanoma associated antigens (TRP2, MAGE-1, MAGE-3, gp100, tyrosinase, MART-1, HSP-70, beta-HCG), human papilloma virus antigens including E1, E2, E6 and E7 derived from HPV-16, -18, -31, -35 or -45, CEA tumor antigen, normal or mutated ras protein, normal or mutated p53, Muc1, and pSA, as well as antigens well known in the art, which are derived from the followings: cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, Addison's disease, immunogens, allergen, cancers including solid and blood borne tumors, acquired immune deficiency syndrome, and factors involved in transplant rejection, such as kidney, heart, pancreas, lung, bone, and liver transplant rejections; and antigens inducing autoimmunity.

Therefore, the target protein produced by the surface expression method of the present invention may be used in various applications. These applications include effective production of antibodies and enzymes, as well as production of peptide libraries for screening antigens, adhesion or adsorption proteins and new physiologically active substances.

In another aspect, the present invention provides a method of expressing a target protein on the surface of a Gram-negative or Gram-positive host cell, the method including steps of: (a) constructing a recombinant vector by inserting a gene encoding the target protein into the surface expression vector; (b) transforming the Gram-negative or Gram-positive host cell with the recombinant vector; and (c) expressing the target protein on the surface of the transformed host cell by culturing the transformed host cell.

Specifically, the present invention provides the surface expression vector pKV-Pald-pgsA-HPV16E7_Pgm-pgsA-EGFP which co-expresses two different target proteins on the microbial surface using an aldolase promoter and galactose mutarotase promoter derived from *Lactobacillus casei*.

In particular, the aldolase promoter and galactose mutarotase promoter derived from *Lactobacillus casei* were used in one example, but either constructing a vector using an aldolase promoter and galactose mutarotase promoter derived from another strain, which have a sequence homology of at least 80% to the nucleotide sequences of the aldolase promoter and galactose mutarotase promoter derived from *Lactobacillus casei*, or expressing foreign proteins on the microbial surface using the constructed vector, is also included in the scope of the present invention.

In one example of the present invention, whether proteins are efficiently expressed on the surface of lactic acid bacteria was examined using HPV protein E7 and enhanced green fluorescent protein (EGFP) selected as model proteins.

The "HPV16E7" is an oncogenic HPV type 16 gene that causes cancer, and E7 proteins are all involved in HPV-mediated cellular immortalization and cell transformation. The E7 protein induces hyperphosphorylation of Rb protein by direct binding thereto, and this E7 protein derived from HPV is a specific target capable of killing only HPV-infected cancer cells, and is used as a drug target in the treatment of HPV-induced cancer. In addition, the "enhanced green fluorescent protein (EGFP)" is a gene that emits green light in vivo to enable easy observation of cells expressing the corresponding protein, and has the advantage of being capable of being observed under a fluorescence microscope. GFP is a green fluorescent protein originating from jellyfish (*Aequorea victoria*) and has been used as an important marker for gene expression in various research fields. EGFP is a mutant of GFP, results from substitution of leucine for phenylalanine at position 64 in the amino acid sequence of GFP and substitution of threonine for serine at position 65, and has the advantage of showing a stronger fluorescent signal than the original GFP.

The present inventors constructed a surface expression vector by inserting HPV16E7 and EGFP genes into a vector, transformed *Lactobacillus casei* with the surface expression vector, and then cultured the transformed *Lactobacillus casei* to induce protein expression, and obtained proteins by collecting a certain amount of the culture. The obtained proteins were analyzed by SDS-PAGE and subjected to Western blotting using anti-EGFP and anti-HPV16E7 antibodies, and as a result, it was confirmed that the HPV16E7 and EGFP proteins were inserted successfully into the constructed surface expression vector pKV-Pald-pgsA-HPV16E7_Pgm-pgsA-EGFP and co-expressed on the cell surface.

In the above-described example, the HPV16E7 and EGFP proteins were used as foreign proteins, but any other proteins, such as enzymes, antigens, antibodies, adhesion proteins, or adsorption proteins, may also be used as foreign proteins.

In addition, two different target proteins are expressed on the cell surface by the surface expression vector of the present invention, and thus the transformed microorganism of the present invention may be used as a vaccine.

In another aspect, the present invention provides a method of producing a microbial vaccine by using lactic acid bacteria transformed with the surface expression vector.

Vaccines are drugs that are used to stimulate the immune system using living organisms for the purpose of preventing diseases. Immune activation refers to a process of efficiently removing antigens by antibody production, stimulation of T-lymphocytes, or stimulation of other immune cells (e.g., macrophages) in organisms. A detailed overview of immunology relating to such details will be easily understood by those skilled in the art (Barrett, J. T., Textbook of Immunology, 1983).

A transformed microorganism vaccine expressing a target protein as an antigen may be administered to mammals, preferably humans.

The preparation of the vaccine composition may be performed using standard techniques. A dose suitable for administration to a subject varies depending on the antigenicity of gene products and may be an amount in which the vaccine can sufficiently induce typical immune responses. The dose can be easily determined through usual experimental procedures. The typical initial dose of the vaccine is 0.001 to 1 mg antigen/kg of body weight. If necessary, the dose can be increased so as to offer a preferred level of protection, or the vaccine is used in a multiple dose. The dose can be determined by those skilled in the art and can also vary depending on various factors such as formulation method, administration mode, the subject's age, body weight and sex, pathological conditions, diet, administration duration, administration route, excretion rate, and response sensitivity.

In order for the vaccine to be effective in producing an antibody, an antigenic substance should be released in vivo so that the antibody-producing mechanism in the vaccinated subject can be realized. Thus, a microbial carrier for a gene product must be preferentially introduced in vivo for immune responses. In order to stimulate a preferred response by an antigen which is presented by the transformant of the present invention, the vaccine is preferably administered orally, by gastrointestinal intubation, or directly to the intestines or lungs in the form of aerosol, even though administration methods such as intravenous injection, intramuscular injection, or subcutaneous injection are also possible.

For oral administration of the vaccine composition to a subject, the vaccine composition is preferably provided in a lyophilic form, for example, a capsule form. The capsule is provided as an enteric coating containing Eudragate S, Eudragate L, cellulose acetate, cellulose phthalate or hydroxypropylmethyl cellulose. The capsule may be used as it is or may be administered after it has been reconstituted into a lyophilic material such as a suspension. The reconstitution is preferably performed in a buffer having a pH value suitable for the survival of the transformed microorganism. In order to protect the transformed microorganism and the vaccine from gastric acid, it is preferable to administer a sodium bicarbonate formulation every time before administering the vaccine. The vaccine can be selectively prepared for parenteral administration, intranasal administration or intramammary administration.

The transformed lactic acid bacteria containing the promoters of the present invention and containing the genes encoding the target proteins capable of acting as antigens may exhibit the desired efficacy while forming colonies in the mucous membrane of the digestive tract, so that the desired efficacy can be obtained. Also, the above-described lactic acid bacteria may co-administer the selected antibiotics in the vector for smooth colony formation while maintaining the desired transformation properties, and may control the development of undesired lactic acid bacteria having no vector, which can be developed during cell division in the transformant. The process for selection of the antibiotics can be easily performed using any conventional technique known in the art, and the selected antibiotics, which may be used in the above process, may vary depending on the antibiotic genes contained in the expression vector.

In addition, in the present invention, improvement of the surface expression vector (pKV-Pald-PgsA-EGFP) constructed in Example 4 below was performed using PgsA gene fragments so that it could more stably exhibit a high gene expression level in the lactic acid bacteria host.

First, among PgsA fragments, PgsA fragments containing 1-60 a.a, 1-70 a.a, 1-80 a.a, 1-100 a.a and 1-188 a.a, respectively, were obtained by performing PCR using the surface expression vector (pKV-Pald-PgsA-EGFP) as a template and the primers of SEQ ID NOs: 11 to 20.

As a result, DNA fragments, containing an aldolase promoter and the respective PgsA motif fragments, were obtained. Each of the DNA fragments contained an SphI restriction enzyme site at the 5' end thereof and a BamHI restriction enzyme site at the 3' end thereof. Each of the obtained DNA fragments was treated with SphI and BamHI to obtain fragments. In addition, it was confirmed that the PgsA1 to A5 motif fragments had the nucleotide sequences of SEQ ID NOs: 21 to 25, respectively.

Meanwhile, among PgsA fragments, PgsA fragments containing 25-60 a.a, 25-70 a.a and 25-100 a.a, respectively, were obtained by performing PCR using the surface expression vector as a template and the primers of SEQ ID NOs: 26 to 31.

As a result, DNA fragments containing the respective PgsA motif fragments were obtained. Each of the fragments contained an EcoRV restriction enzyme site at the 5' end thereof and a BamHI restriction enzyme site at the 3' end thereof. The obtained DNA fragments were treated with EcoRV and BamHI to obtain fragments. In addition, it was confirmed that the PgsA motif fragments had the nucleotide sequences of SEQ ID NOs: 32 to 34, respectively.

An object of the present invention is to provide a method including: selecting an outer membrane protein, which is derived from a *Bacillus* sp. strain and involved in the synthesis of poly-gamma-glutamate, as a new surface anchoring motif capable of expressing a large amount of a foreign protein on the microbial surface; constructing a surface expression vector capable of expressing a foreign protein or peptide on the microbial surface using the selected outer membrane protein; and efficiently expressing a foreign protein on the surface of a transformant obtained using the surface expression vector.

To achieve the above object, the present invention provides a microbial surface expression vector containing the gene pgsA encoding a poly-gamma-glutamate synthetase complex, and a strain transformed with the vector.

To achieve the above object, the present invention also provides a method of expressing a foreign protein on the surface of the transformed strain using the microbial surface expression vector.

The protein encoded by the gene pgsA is an outer membrane protein present in *Bacillus* sp., and is a protein which is involved in the synthesis of poly-gamma-glutamate, which is an edible, water-soluble, anionic and biodegradable polymer produced from *Bacillus subtilis* IF03336 (Natto; Biochem. Biophy. Research Comm., 263, 6-12, 1999), *Bacillus licheniformis* ATCC9945 (Biotech. Bioeng. 57(4), 430-437, 1998), *Bacillus anthracis* (J. Bacteriology, 171, 722-730, 1989), etc.

The outer membrane proteins isolated from *Bacillus subtilis* IF03336 consist of a total of 922 amino acids and are composed of pgsB, pgsC and pgsA. pgsB consists of 393 amino acids, pgsC consists of 149 amino acids, and pgsA consists of 380 amino acids. Ashiuchi et al. cloned the poly-gamma-glutamate synthetase gene derived from *Bacillus subtilis*, transformed the gene into *E. coli*, and observed the synthesis of the gene in the *E. coli* [Ashiuchi et al., Biochem. Biophy. Res. Communications, 263: 6-12 (1999)].

However, the detailed role and function of the pgsA protein of the poly-gamma-glutamate synthetase complex have not yet been found. However, among the proteins of the complex, pgsB is an amide ligase system, and the specific amino acids at the N-terminus of pgsB interact with the cell membrane or cell wall, and pgsA has hydrophilic specific amino acid sequences at the N-terminus and C-terminus thereof. Thus, it is presumed that these amino acids have secretion signals, which can pass through the inner cell membrane with the help of pgsB, and targeting and adhesion signals.

The study conducted by the present inventors revealed that the outer membrane proteins which are involved in the synthesis of poly-gamma-glutamate has many advantages as a surface anchoring motif which expresses a foreign protein on the cell surface due to the primary amino acid sequence structures and characteristics thereof. The advantages are as follows. First, the outer membrane proteins which are involved in the synthesis of poly-gamma-glutamate may be expressed in large amounts on the cell surface for the synthesis and extracellular secretion of poly-gamma-glutamate. Second, the expressed outer membrane proteins which are involved in the synthesis of poly-gamma-glutamate are stably maintained even in the resting phase of the cell cycle. Third, structurally, pgsA protrudes from the cell surface. Fourth, the outer membrane proteins which are involved in the synthesis of poly-gamma-glutamate originate from the surfaces of Gram-positive bacteria and may be stably expressed on the surfaces of not only various Gram-positive bacteria but also Gram-negative bacteria.

An object of the present invention is to provide a useful vector capable of expressing a foreign protein on the bacterial surface using the characteristics of an outer membrane protein which is involved in the synthesis of poly-gamma-glutamate. In particular, the surface expression vector for expressing a target protein according to the present invention includes a secretion signal and a targeting signal, which are contained in the primary sequence of the outer membrane protein which is involved in the synthesis of poly-gamma-glutamate.

Another object of the present invention is to provide a method of expressing a foreign protein on the microbial surface using a surface expression vector which uses the characteristics of an outer membrane protein which is involved in the synthesis of poly-gamma-glutamate. In particular, the present invention provides a method for producing a foreign protein, which enables the foreign protein to be efficiently used without a cell disruption or protein isolation/purification process by expressing the foreign protein on the microbial surface using an outer membrane protein which is involved in the synthesis of poly-gamma-glutamate.

The scope of the present invention includes all surface expression vectors containing all kinds of genes which are involved in the synthesis of poly-gamma-glutamate, including genes encoding outer membrane proteins which are derived from a *Bacillus* sp. strain and involved in the synthesis of poly-gamma-glutamate.

In addition, the surface expression vector containing a poly-gamma-glutamate synthetase gene according to the present invention may be applied to all types of strains to express a foreign protein on the microbial surface. Preferably, the surface expression vector may be applied to Gram-negative bacteria, more preferably *E. coli, Salmonella typhi, Salmonella typhimurium, Vibrio cholera, Mycobacterium bovis*, and *Shigella*, and to Gram-positive bacteria, preferably *Bacillus, Lactobacillus, Lactococcus, Staphylococcus, Lysteria monocytogenes*, and *Streptococcus*. Methods all types of foreign protein using; the above strains are included witan the scope of the present invention.

If necessary, restriction enzyme recognition sites may be inserted into the N-terminus or C-terminus of the poly-gamma-glutamate synthetase gene, and surface expression vectors having these restriction enzyme sites inserted therein are all included within the scope of the present invention.

Specifically, the present invention provides the surface expression vectors pKV-Pald-pgsA1 to pKV-Pald-pgsA8 which contain the poly-gamma-glutamate synthetase gene pgsA derived from a *Bacillus* sp. strain and into which various foreign genes may be easily cloned using restriction enzyme recognition sites inserted into the C-terminus of pgsA.

The present invention provides the surface expression vectors pKV-Pald-pgsA1 to pKV-Pald-pgsA8 which contain the outer membrane complex pgsA among outer membrane protein complexes involved in the synthesis of poly-gamma-glutamate, and may express, on the surface of Gram-positive bacteria, an EGFP protein in the form of a fusion protein obtained by linking the N-terminus of the EGFP protein to the C-terminus of pgsA.

In particular, in one example of the present invention, the outer-membrane protein gene pgsA which is involved in the synthesis of poly-gamma-glutamate was obtained from *Bacillus subtilis* var. Chungkookjang (KCTC 0697BP), but constructing a vector using pgsA obtained from any *Bacillus* sp. strain, which produces poly-gamma-glutamate, or expressing a foreign protein on the microbial surface using the vector, is also included within the scope of the present invention. For example, constructing a vector using a pgsA gene derived from any strain, which has a sequence homology of at least 80% to the nucleotide sequence of the pgsA gene present in *Bacillus subtilis* var. Chungkookjang, or expressing a foreign protein on the microbial surface using the vector, is also included within the scope of the present invention.

In another example of the present invention, whether a protein is efficiently expressed on the *E. coli* cell surface was examined using enhanced Green fluorescent protein (EGFP) selected as a model protein. The "enhanced green fluorescent protein (EGFP)" is a gene that emits green light in vivo to enable easy observation of cells expressing the corresponding protein, and has the advantage of being capable of being observed under a fluorescence microscope. GFP is a green fluorescent protein originating from jellyfish (*Aequorea victoria*) and has been used as an important marker for gene expression in various research fields. EGFP is a mutant of GFP, results from substitution of leucine for phenylalanine at position 64 in the amino acid sequence of GFP and substitution of threonine for serine at position 65, and has the advantage of showing a stronger fluorescent signal than the original GFP The present inventors constructed surface expression vectors by inserting the EGFP gene into the above-described constructed recombinant vectors pKV-Pald-pgsA1 to pKV-Pald-pgsA8, transformed *Lactobacillus casei* with each of the surface expression vectors, and then cultured the transformed *Lactobacillus casei* to induce protein expression, and obtained a protein by collecting a certain amount of the culture. The obtained protein was analyzed by SDS-PAGE and subjected to Western blotting using anti-EGFP antibody, and as a result, it was confirmed that the EGFP protein was inserted successfully into the constructed recombinant vectors pKV-Pald-pgsA1 to pKV-Pald-pgsA8 and expressed on the cell surface.

Hereinafter, the present invention will be described in more detail with reference to examples. It will be obvious to those skilled in the art that these examples serve merely to describe the present invention in more detail, and the scope of the present invention according to the subject matter of the present invention is not limited by these examples.

In addition, in the following examples, EGFP protein was used as a foreign protein, but any other proteins such as enzymes, antigens, antibodies, adhesion proteins or adsorption proteins may also be used as foreign proteins.

In addition, in the following examples, surface expression vectors for application to Gram-positive bacteria were constructed and *Lactobacillus casei* was used as host cells, but it will be obvious to those skilled in the art that any Gram-positive bacteria other than *Lactobacillus casei* may be used as host cells, and Gram-negative bacteria and other bacteria other than Gram-positive bacteria may be transformed with the surface expression vectors.

Example 1: Construction of Surface Expression Vector pKV-Pald-pgsA-HPV16E7_Pgm-pgsA-EGFP for Co-Expression of Two Antigens To construct a surface expression vector for co-expression of two antigens, using the surface expression vector pKV-Pald-pgsA-E7 (pKV-Pald-pgsA380L-HPV16E7; see Korean Patent No. 10-1471043), a gene encoding Pgm-pgsA-EGFP was inserted into the C-terminus of Pald-pgsA-HPV16E7 to obtain the vector pKV-Pald-pgsA-HPV16E7 Pgm-pgsA-EGFP capable of co-expressing two different target proteins on the surface of lactic acid bacteria.

First, to construct an EGFP expression vector, the HPV16 E7 gene fused with pgsA pKV-Pald-PgsA-E7 (see Korean Patent No. 10-1471043) was removed, and a gene encoding EGFP was inserted into the vector.

Using the synthesized EGFP gene fragment, PCR was using the primers of SEQ ID NO: 3 and SEQ ID NO: 4.

SEQ ID NO 3:
5'-TGGTGGATCCGTGAGCAAGGGCGAGGAGCTG-3'

SEQ ID NO 4:
5'-TGACTCTAGAACTAGTGTCGACGGTACCTTACTTGTACAGCTCGTCC-3'

As a result, a 755-bp EGFP gene fragment was obtained, which contains a BamHI restriction enzyme site at the 5' end thereof and an XbaI restriction enzyme site at the 3' end thereof. The obtained DNA fragment was treated with BamHI and XbaI restriction enzymes, the vector pKV-Pald-pgsA-E7 was cleaved with BamHI and XbaI to remove the HPV16 E7 gene region, and then the EGFP gene and the cleaved vector were ligated to each other to obtain pKV-Pald-pgsA-EGFP.

In addition, in order to replace the aldolase promoter in the pKV-Pald-pgsA-EGFP vector by a galactose mutarotase promoter, the *Lactobacillus casei* genome was subjected to PCR using the primers of SEQ ID NO: 5 and SEQ ID NO: 6 to obtain a galactose mutarotase promoter fragment containing an SphI restriction enzyme site at the 5' end thereof and a XbaI restriction enzyme site at the 3' end thereof. The obtained DNA fragment was treated with SphI and XbaI restriction enzymes, and the vector pKV-Pald-pgsA-EGFP was also cleaved with the same restriction enzymes to remove the aldolase promoter region, and then the galactose mutarotase promoter and the cleaved promoter were ligated to each other to obtain pKV-Pgm-pgsA-EGFP.

SEQ ID NO 5:
5'-TACGGCATGCTTGAATTGGTTTCTTACGAT-3'

SEQ ID NO 6:
5'-TACGCTCGAGGTTGAATTACCTCCTAATAG-3'

Finally, in order to insert Pgm-pgsA-EGFP into the C-terminus of the E7 region of the pKV-Pald-pgsA-E7 vector, PCR was performed using the pKV-Pgm-pgsA-EGFP vector as a template and the primers of SEQ ID NO: 7 and SEQ ID NO: 8.

SEQ ID NO 7:
5'-GCGCGAATTCTTGAATTGGTTTCTTACGA-3'

SEQ ID NO 8:
5'-GCGCTGCGCATTACTTGTACAGCTCGTC-3'

As a result, a 2,608-bp fragment including the Pgm-pgsA-EGFP gene was obtained, which contains an EcoRI restriction enzyme site at the 5' end thereof and an FspI restriction enzyme site at the 3' end thereof. The obtained DNA fragment, which is a gene encoding Pgm-pgsA-EGFP, was inserted into the surface expression vector pKV-Pald-pgsA-HPV16E7 using the EcoRI and FspI restriction enzyme sites to obtain pKV-Pald-pgsA-HPV16E7_Pgm-pgsA-EGFP which is a 1,1171-bp fragment (FIGS. 1 and 2).

Example 2: Analysis of Expression of Two Target Proteins by Western Blotting

In this Example, *Lactobacillus casei* was transformed with the surface expression vector pKV-Pald-pgsA-HPV16E7_Pgm-pgsA-EGFP constructed in Example 1. The transformed recombinant *Lactobacillus casei* was cultured, and expression of HPV16E7 and EGFP proteins on the surface thereof was analyzed. Whether the HPV16E7 and EGFP proteins were expressed on the transformed recombinant *Lactobacillus casei* was examined by Western blotting.

The recombinant *Lactobacillus casei* transformed with the surface expression vector of the present invention was stationary-cultured in MRS medium (*Lactobacillus* MRS, Becton Dickinson and Company Sparks, USA) at 30° C. to induce expression of the HPV16E7 and EGFP proteins.

Expression of the fusion proteins was analyzed by subjecting the cultured *Lactobacillus casei* whole cells to SDS-polyacrylamide gel electrophoresis and to Western blotting using a specific antibody against each of pgsA, HPV16E7 and EGFP.

Specifically, the recombinant *Lactobacillus casei* whole cells on which protein expression was induced were denatured with proteins obtained at the same cell concentration to prepare a sample. The sample was analyzed by SDS-polyacrylamide gel electrophoresis, and then the fractionated proteins were transferred to a PVDF (polyvinylidene-difluoride) membrane (Bio-Rad). The PVDF membrane having the proteins transferred thereto was blocked in blocking buffer (50 mM Tris-HCl, 5% skim milk, pH 8.0) for 1 hour, and then incubated for 1 hour with a 1:1,000 dilution of an anti-rabbit polyclonal primary antibody against each of pgsA, HPV16E7 and EGFP in blocking buffer. After completion of the incubation, the membrane was washed with buffer and incubated for 1 hour with a 1:10,000 dilution of HRP (horseradish peroxidase)-conjugated anti-rabbit secondary antibody in blocking solution. After completion of the incubation, the membrane was washed with buffer, and the washed membrane was color-developed with a substrate (Lumigen PS-3 acridan, $H_2O_2$) for about 2 minutes. Then, specific binding between the specific antibody against each of pgsA, HPV16E7 and EGFP and the fusion protein was visualized by a CCD camera (FIG. 3).

Figure 3:
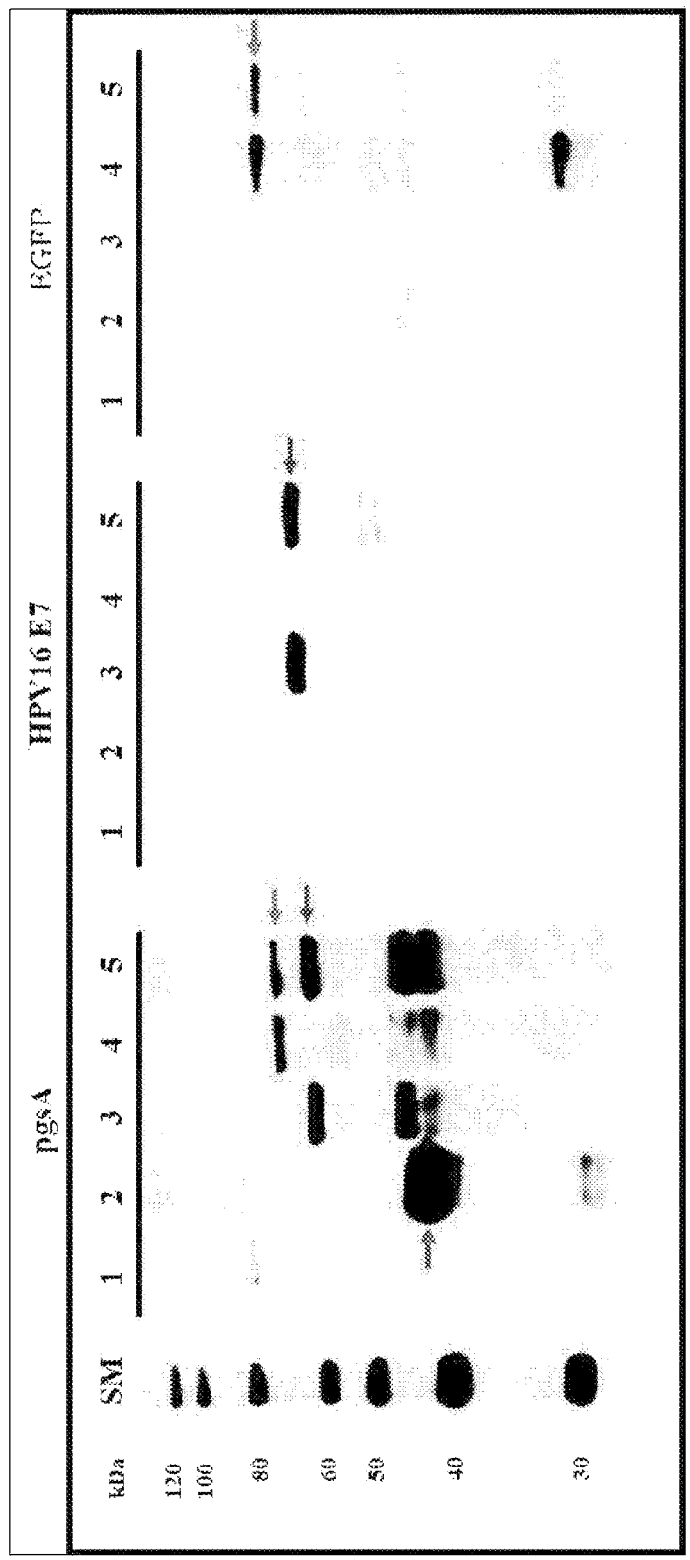
FIG. 3 shows the results of Western blotting performed to measure the expression of HPV16 E7 and EGFP proteins on a microorganism transformed with the surface expression vector of the present invention.

FIG. 3 shows the results of performing Western blotting to analyze the expression levels of pgsA, HPV16 E7 and EGFP in the recombinant *Lactobacillus casei* whole cells transformed with the surface expression vector of the present invention. In FIG. 3, Lane SM represents a protein size marker, lane 1 represents *Lactobacillus casei* (empty vector), lane 2 represents expression on *Lactobacillus casei* (pKV-Pald-pgsA), lane 3 represents expression on *Lactoba-* cillus casei (pKV-Pald-pgsA-HPV16E7), lane 4 represents expression on *Lactobacillus casei* (pKV-Pgm-pgsA-EGFP), and lane 5 represents expression on *Lactobacillus casei* (pKV-Pald-pgsA-HPV16E7 Pgm-pgsA-EGFP).

It was confirmed that the surface expression vector pKV-Pald-pgsA-HPV16E7_Pgm-pgsA-EGFP (Lane 5) co-expressed the two different proteins, unlike the surface expression vectors pKV-Pald-pgsA-HPV16E7 (Lane 3) and pKV-Pgm-pgsA-EGFP (Lane 4) for expressing a single target protein. This indicates that the two different promoters can stably co-express the respective target proteins stably without interfering with each other in the surface expression vector.

Example 3: Observation of Expression of Two Target Proteins on Microbial Surface by Confocal Fluorescence Microscopy In order to examine the expression level of the surface expression vector of the present invention, fluorescence images were observed by confocal microscopy (Carl Zeiss LSM800).

The recombinant *Lactobacillus casei* transformed with the surface expression vector (pKV-Pald-pgsA-HPV16E7_Pgm-pgsA-EGFP) of the present invention was stationary-cultured in MRS medium (*Lactobacillus* MRS, Becton Dickinson and Company Sparks, USA) at 30° C. to induce the HPV16E7 and EGFP proteins on the cell surface. Next, each protein was allowed to bind to each specific antibody, and then HPV16E7 was immunostained with Alexa594 (red), and EGFP was immunostained with Alexa488 (green). Then, expression of each antigen on the cell surface was observed by confocal microscopy.

Figure 4:
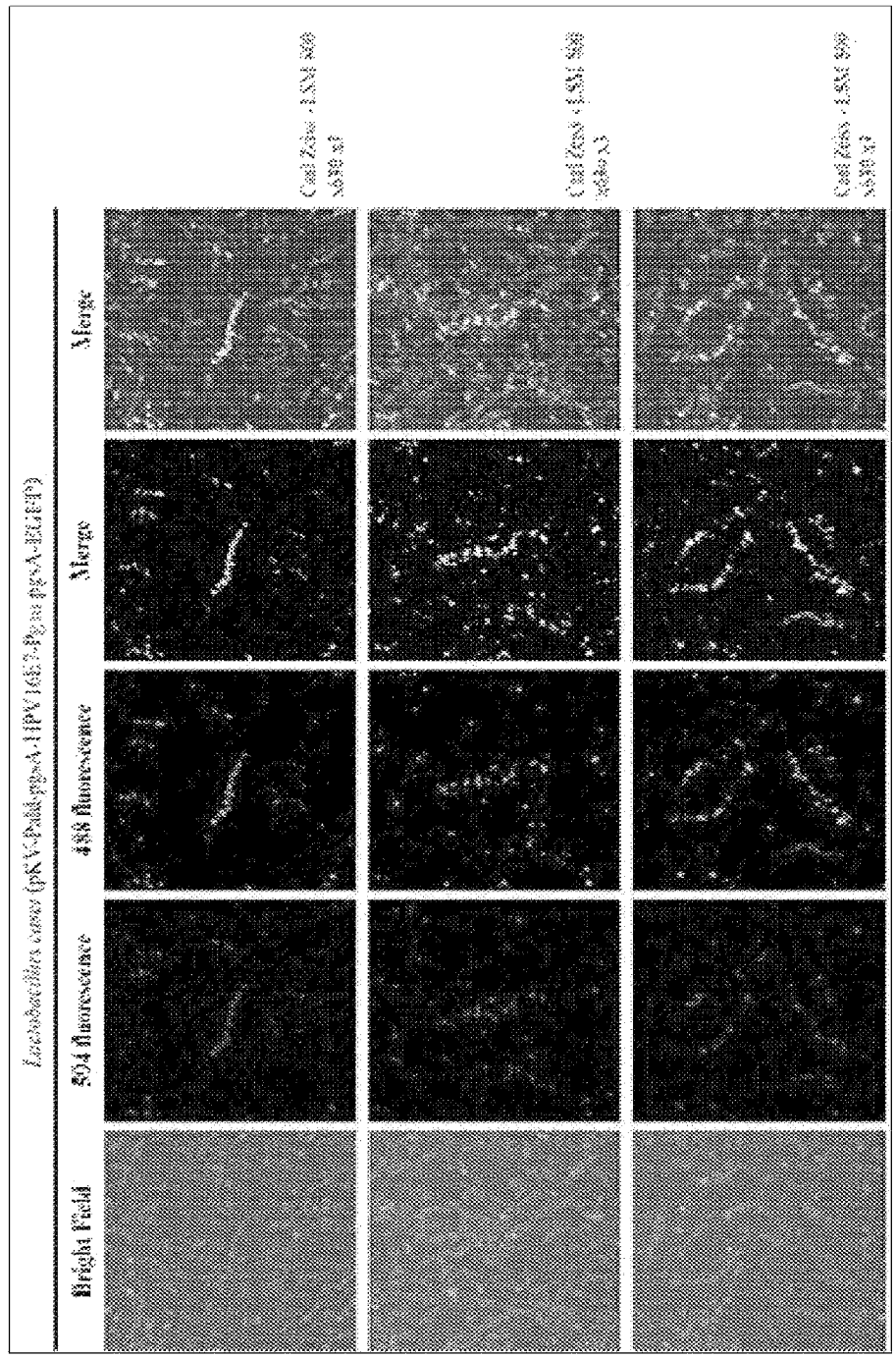
FIG. 4 shows the results of confocal fluorescence microscopic observation that indicate that two different antigens are stably co-expressed on the surface of lactic acid bacteria by the surface expression vector of the present invention.

As a result, as shown in FIG. 4, it could be confirmed that two fluorescent colors were stably co-expressed in the recombinant *Lactobacillus casei* transformed with the surface expression vector of the present invention.

Thus, it is expected that the surface expression vector of the present invention may be transformed into lactic acid bacteria, and may be used as a method of efficiently co-expressing two different target proteins within a short time, which does not require a strain-detoxifying step, unlike a conventional vaccine production method.

Example 4: Construction of Surface Expression Vector pKV-Pald-pgsA-EGFP

To construct a vector for EGFP expression, using the surface expression vector pKV-Pald-PgsA-E7 (see Korean Patent No. 10-1471043), a gene encoding the EGFP protein was inserted into the C-terminus of PgsA of the surface expression vector to obtain the vector pKV-Pald-PgsA-EGFP capable of expressing the EGFP protein on the surface of lactic acid bacteria.

First, the HPV16 E7 gene fused with pgsA in the pKV-Pald-PgsA-E7 vector was removed, and a gene encoding EGFP was inserted into the vector. Using the synthesized EGFP gene fragment as a template, PCR was performed using the primers of SEQ ID NOs: 9 and 10.

SEQ ID NO 9:
5' TGGTGGATCCGTGAGCAAGGGCGAGGAGCTG 3'

SEQ ID NO 10:
5' TGACTCTAGAACTAGTGTCGACGGTACCTTACTTGTACAGCTCGTCC 3'

As a result, a 755-bp fragment containing the EGFP gene was obtained, which contains a BamHI restriction enzyme site at the 5' end thereof and an XbaI restriction enzyme site at the 3' end thereof. The obtained DNA fragment was cleaved by treatment with BamHI and XbaI restriction enzymes to obtain a 741-bp fragment.

pKV-Pald-PgsA-E7 was cleaved with BamHI and XbaI to remove the HPV16 E7 gene region and to obtain the vector region.

Figure 5:
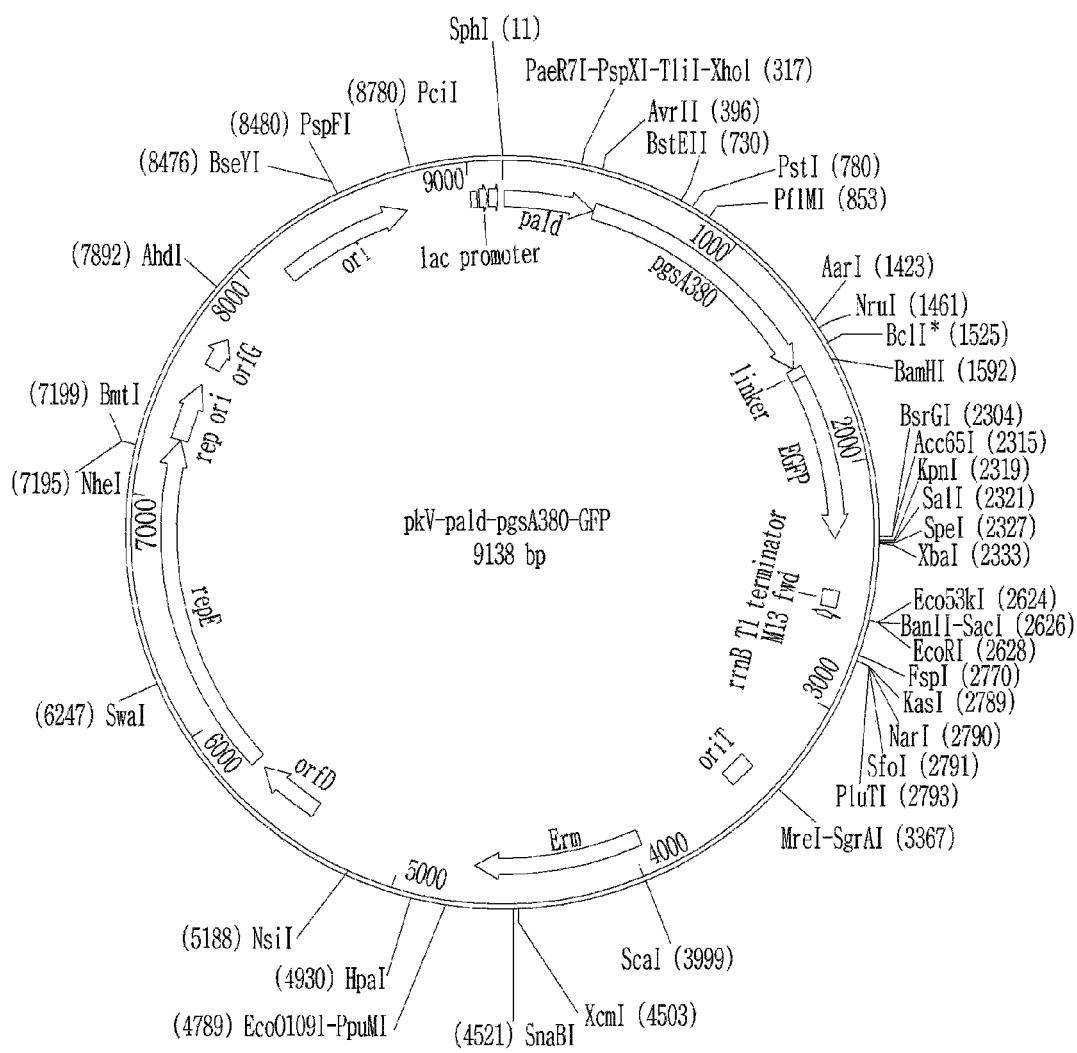
FIG. 5 shows a genetic map of the surface expression vector pKV-Pald-PgsA-EGFP according to the present invention, which uses Lactobacillus casei as a host.
Figure 6:
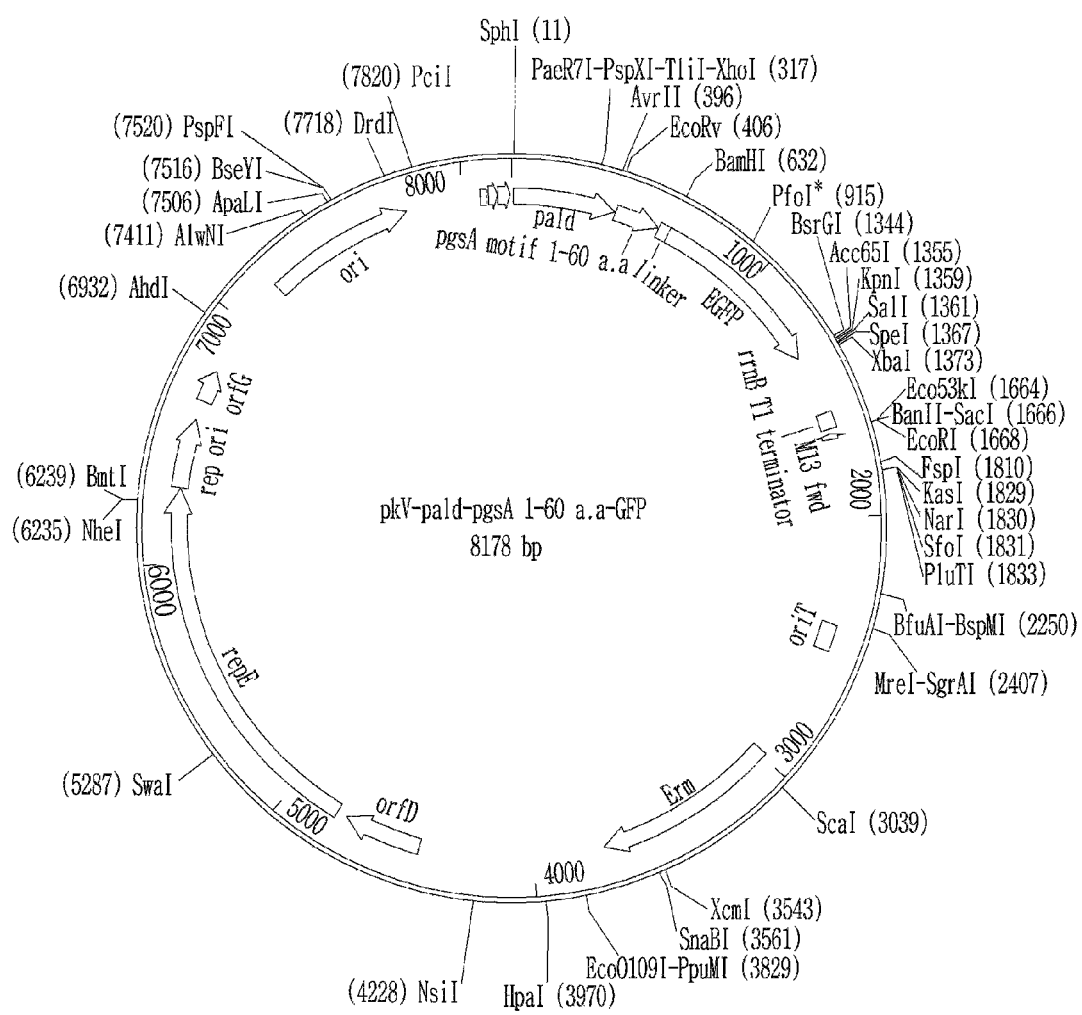
FIG. 6 shows a genetic map of the surface expression vector pKV-Pald-pgsA1 (pgsA motif 1-60 a.a)-EGFP according to the present invention, which uses Lactobacillus casei as a host.
Figure 7:
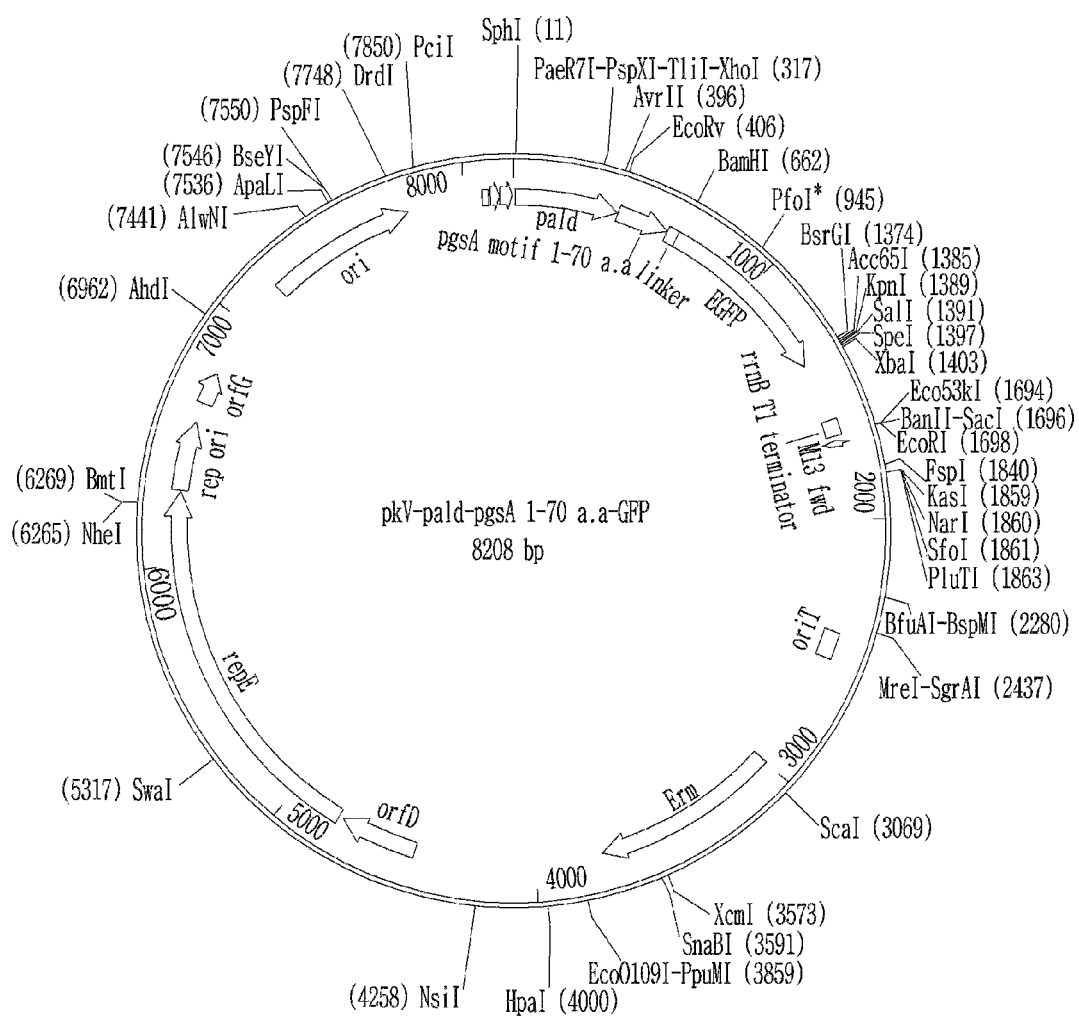
FIG. 7 shows a genetic map of the surface expression vector pKV-Pald-pgsA2 (pgsA motif 1-70 a.a)-EGFP according to the present invention, which uses Lactobacillus casei as a host.
Figure 8:
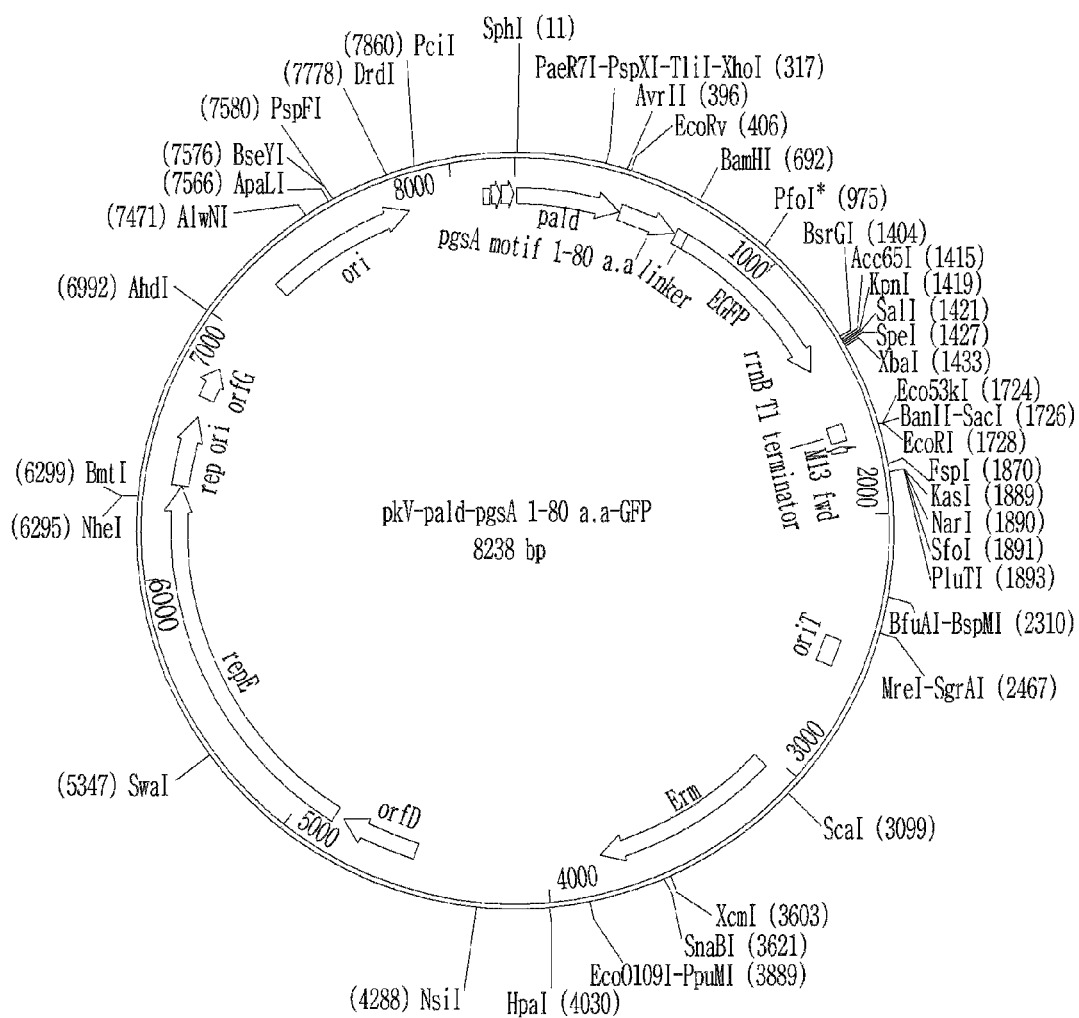
FIG. 8 shows a genetic map of the surface expression vector pKV-Pald-pgsA3 (pgsA motif 1-80 a.a)-EGFP according to the present invention, which uses Lactobacillus casei as a host.
Figure 9:
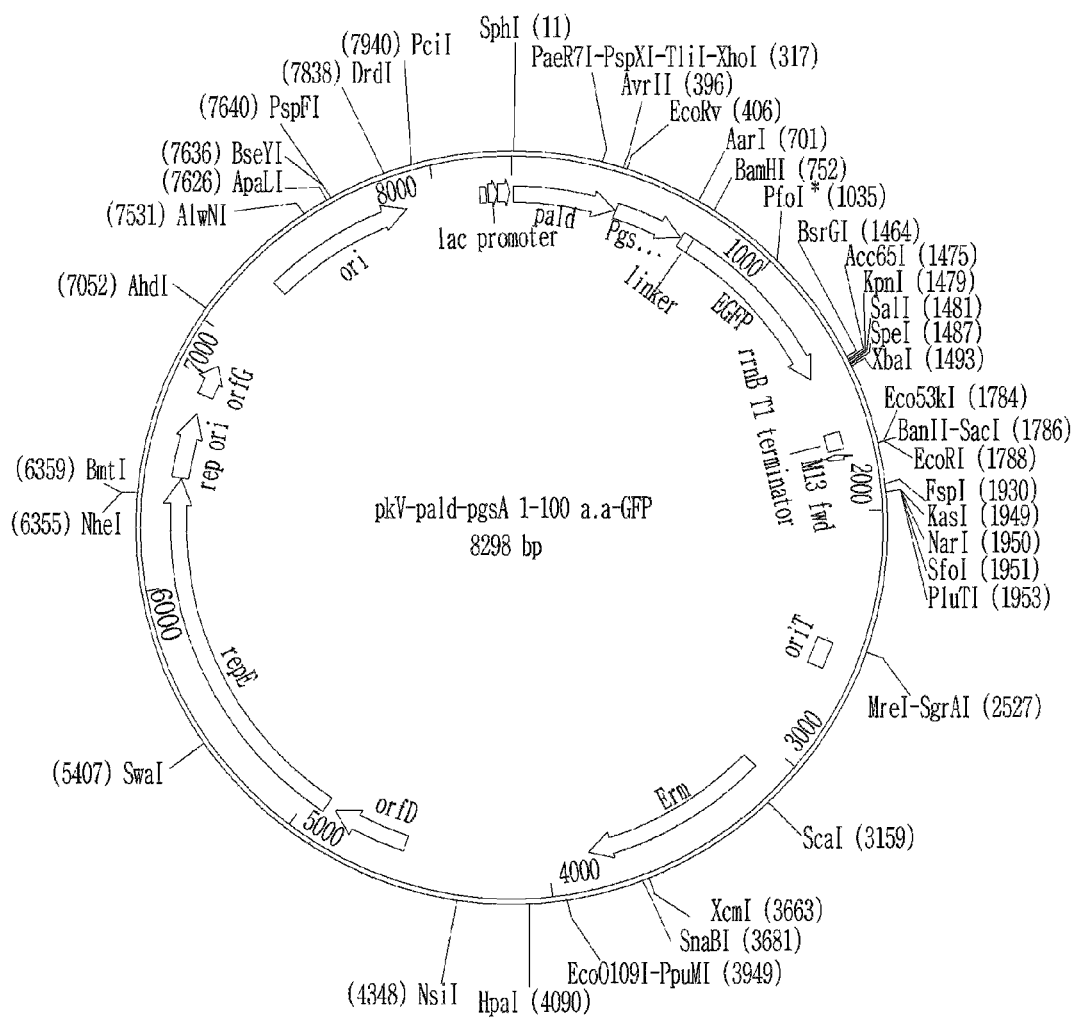
FIG. 9 shows a genetic map of the surface expression vector pKV-Pald-pgsA4 (pgsA motif 1-100 a.a)-EGFP according to the present invention, which uses Lactobacillus casei as a host.
Figure 10:
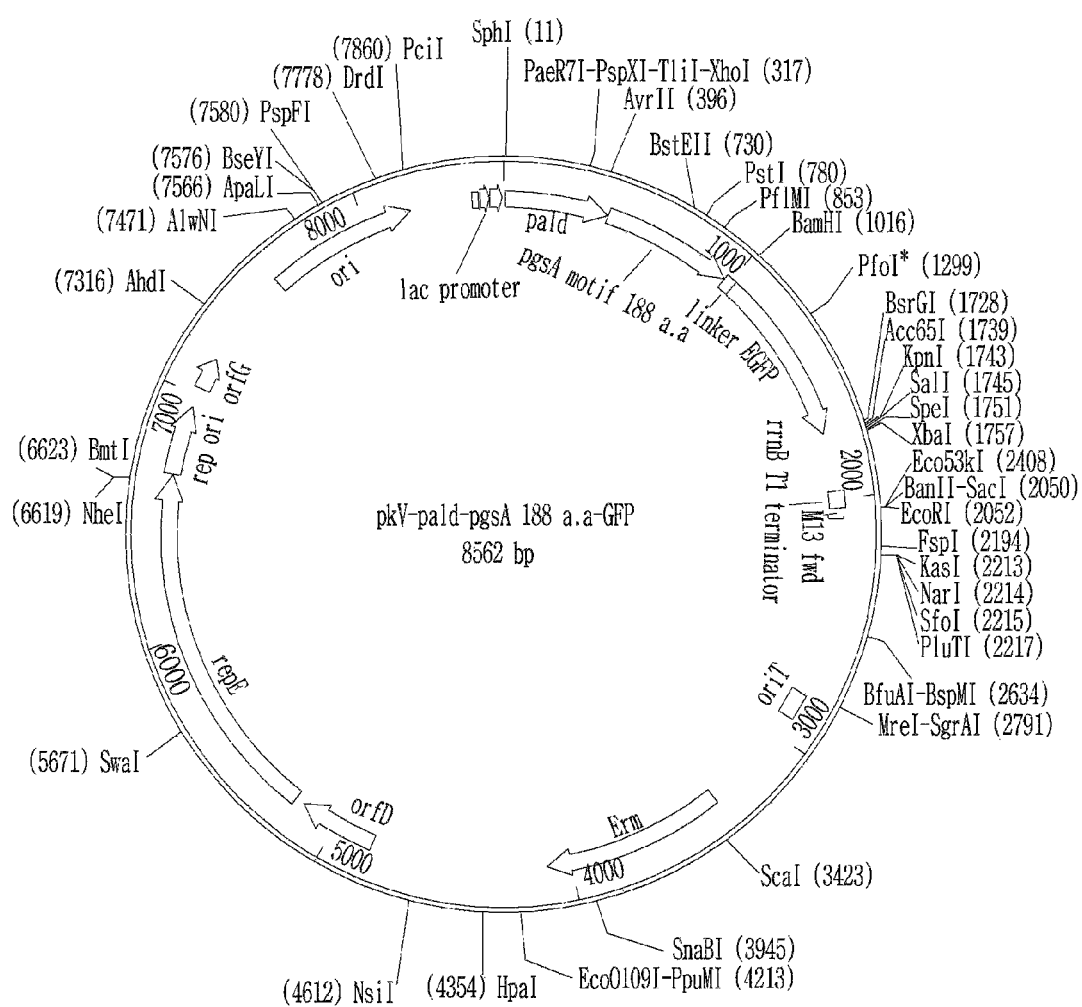
FIG. 10 shows a genetic map of the surface expression vector pKV-Pald-pgsA5 (pKV-pgsA 1-188 a.a)-EGFP according to the present invention, which uses Lactobacillus casei as a host.

The E7 gene-containing DNA fragment cleaved with BamHI and XbaI was ligated with the vector cleaved with the same restriction enzymes, thus constructing pKV-Pald-PgsA-EGFP (FIG. 5).

Example 5: Improvement of PgsA Motif in Surface Expression Vector

In this Example, improvement of the PgsA gene fragment in the surface expression vector (pKV-Pald-PgsA-EGFP) constructed in Example 4 was performed so that the vector could exhibit a high expression level in the lactic acid bacteria host.

First, among PgsA fragments, PgsA fragments containing 1-60 a.a, 1-70 a.a, 1-80 a.a, 1-100 a.a and 1-188 a.a, respectively, were obtained by performing PCR using the surface expression vector pKV-Pald-PgsA-EGFP as a template and the following primers.

PgsA motif 1-60 a.a
SEQ ID NO 11:
5' TCGAGCATGCAATACCCACTTATTGCGATTTGCT 3'

SEQ ID NO 12:
5' TACGGGATCCACCAGAACCACCAGAACCACCAGAACCACCAGAACC ACCTGAGAGTACGTCGTCAGAATACGTT 3'

PgsA motif 1-70 a.a
SEQ ID NO 13:
5' TCGAGCATGCAATACCCACTTATTGCGATTTGCT3'

SEQ ID NO 14:
5' TACGGGATCCACCAGAACCACCAGAACCACCAGAACCACCAGAACC ACCTCCCATCATAATATCGCCTACAAAT 3'

PgsA motif 1-80 a.a
SEQ ID NO 15:
5' TCGAGCATGCAATACCCACTTATTGCGATTTGCT3'

SEQ ID NO 16:
5' TACGGGATCCACCAGAACCACCAGAACCACCAGAACCACCAGAACC ACCTTTTTGCTCCGTTACTTTTTCAACA 3'

PgsA motif 1-100 a.a
SEQ ID NO 17:
5' TCGAGCATGCAATACCCACTTATTGCGATTTGCT3'

SEQ ID NO 18:
5' TACGGGATCCACCAGAACCACCAGAACCACCAGAACCACCAGAACC ACCTGCTACATAATCCGAGGCTCTAAAG 3'

PgsA motif 1-188 a.a
SEQ ID NO 19:
5' TCGAGCATGCAATACCCACTTATTGCGATTTGCT 3'

SEQ ID NO 20:
5' TACGGGATCCACCAGAACCACCAGAACCACCAGAACCACCAGAACC ACCGACTTTCTGGTACGAAATTTTCTTT 3'

As a result, DNA fragments containing an aldolase promoter and the respective PgsA motif fragments were obtained. Each of the DNA fragments contained an SphI restriction enzyme site at the 5' end thereof and a BamHI restriction enzyme site at the 3' end thereof. Each of the obtained DNA fragments was treated with SphI and BamHI to obtain fragments. In addition, it was confirmed that the PgsA1 to PgsA5 motif fragments had the following nucleotide sequences, respectively.

```
PgsA 1-60 a.a fragment sequence (PgsA1)
SEQ ID NO 21:
5'ATGAAAAAAGAACTGAGCTTTCATGAAAAGCTGCTAAAGCTGACAA
AACAGCAAAAAAAGAAAACCAATAAGCACGTATTTATTGCCATTCCGAT
CGTTTTTGTCCTTATGTTCGCTTTCATGTGGGCGGGAAAAGCGGAAACG
CCGAAGGTCAAAACGTATTCTGACGACGTACTCTCA 3'

PgsA 1-70 a.a fragment sequence (PgsA2)
SEQ ID NO 22:
5'ATGAAAAAAGAACTGAGCTTTCATGAAAAGCTGCTAAAGCTGACAAA
ACAGCAAAAAAAGAAACCAATAAGCACGTATTTATTGCCATTCCGATC
GTTTTTGTCCTTATGTTCGCTTTCATGTGGGCGGGAAAAGCGGAAACGC
CGAAGGTCAAAACGTATTCTGACGACGTACTCTCAGCCTCATTTGTAGG
CGATATTATGATGGGA 3'

PgsA 1-80 a.a fragment sequence (PgsA3)
SEQ ID NO 23:
5'ATGAAAAAAGAACTGAGCTTTCATGAAAAGCTGCTAAAGCTGACAAA
ACAGCAAAAAAAGAAACCAATAAGCACGTATTTATTGCCATTCCGATC
GTTTTTGTCCTTATGTTCGCTTTCATGTGGGCGGGAAAAGCGGAAACGC
CGAAGGTCAAAACGTATTCTGACGACGTACTCTCAGCCTCATTTGTAGG
CGATATTATGATGGGACGCTATGTTGAAAAAGTAACGGAGCAAAAA 3'

PgsA 1-100 a.a fragment sequence (PgsA4)
SEQ ID NO 24:
5'ATGAAAAAAGAACTGAGCTTTCATGAAAAGCTGCTAAAGCTGACAAA
ACAGCAAAAAAAGAAACCAATAAGCACGTATTTATTGCCATTCCGATC
GTTTTTGTCCTTATGTTCGCTTTCATGTGGGCGGGAAAAGCGGAAACGC
CGAAGGTCAAAACGTATTCTGACGACGTACTCTCAGCCTCATTTGTAGG
CGATATTATGATGGGACGCTATGTTGAAAAAGTAACGGAGCAAAAAGGG
GCAGACAGTATTTTTCAATATGTTGAACCGATCTTTAGAGCCTCGGATT
ATGTAGCA 3'

PgsA 1-188 a.a fragment sequence (PgsA5)
SEQ ID NO 25:
5'ATGAAAAAAGAACTGAGCTTTCATGAAAAGCTGCTAAAGCTGACAAA
ACAGCAAAAAAAGAAACCAATAAGCACGTATTTATTGCCATTCCGATC
GTTTTTGTCCTTATGTTCGCTTTCATGTGGGCGGGAAAAGCGGAAACGC
CGAAGGTCAAAACGTATTCTGACGACGTACTCTCAGCCTCATTTGTAGG
CGATATTATGATGGGACGCTATGTTGAAAAAGTAACGGAGCAAAAAGGG
GCAGACAGTATTTTTCAATATGTTGAACCGATCTTTAGAGCCTCGGATT
ATGTAGCAGGAAACTTTGAAAACCCGGTAACCTATCAAAAGAATTATAA
ACAAGCAGATAAAGAGATTCATCTGCAGACGAATAAGGAATCAGTGAAA
GTCTTGAAGGATATGAATTTCACGGTTCTCAACAGCGCCAACAACCACG
CAATGGATTACGGCGTTCAGGGCATGAAAGATACGCTTGGAGAATTTGC
GAAGCAAAACCTTGATATCGTTGGAGCGGGATACAGCTTAAGTGATGCG
AAAAAGAAAATTTCGTACCAGAAAGTC 3'
```

The pKV-Pald-PgsA-EGFP was cleaved with SphI and BamHI to remove the aldolase promoter and the PgsA gene region and to obtain the vector region.

Each of the DNA fragments, cleaved with SphI and BamHI and containing an aldolase promoter and the respective PgsA motif fragment genes, was ligated with the vector cleaved with the same restriction enzymes, thus constructing improved vectors (FIGS. 6 to 10).

Meanwhile, among PgsA fragments, PgsA fragments containing 25-60 a.a, 25-70 a.a and 25-100 a.a, respectively, were obtained by performing PCR using the surface expression vector (pKV-Pald-PgsA-EGFP) as a template and the following primers.

```
PgsA motif 25-60 a.a
SEQ ID NO 26:
5' CGCTGGATATCTACATGCACGTATTTATTGCCATTCCG 3'

SEQ ID NO 27:
5'TACGGGATCCACCAGAACCACCAGAACCACCAGAACCACCAGAACCA
CCTGAGAGTACGTCGTCAGAATACGTT 3'

PgsA motif 25-70 a.a
SEQ ID NO 28:
5' CGCTGGATATCTACATGCACGTATTTATTGCCATTCCG 3'

SEQ ID NO 29:
5'TACGGGATCCACCAGAACCACCAGAACCACCAGAACCACCAGAACCA
CCTCCCATCATAATATCGCCTACAAAT 3'

PgsA motif 25-100 a.a
SEQ ID NO 30:
5' CGCTGGATATCTACATGCACGTATTTATTGCCATTCCG 3'
SEQ ID NO 31 :
5'TACGGGATCCACCAGAACCACCAGAACCACCAGAACCACCAGAACCA
CCTGCTACATAATCCGAGGCTCTAAAG 3'
```

As a result, DNA fragments containing the respective PgsA motif fragments were obtained. Each of the fragments contained an EcoRV restriction enzyme site at the 5' end thereof and a BamHI restriction enzyme site at the 3' end thereof. Each of the obtained DNA fragments was treated with EcoRV and BamHI to obtain fragments. In addition, it was confirmed that the PgsA motif fragments have the following nucleotide sequences, respectively.

```
PgsA 25-60 a.a fragment sequence (PgsA6)
SEQ ID NO 32:
5'CACGTATTTATTGCCATTCCGATCGTTTTTGTCCTTATGTTCGCTTT
CATGTGGGCGGGAAAAGCGGAAACGCCGAAGGTCAAAACGTATTCTGAC
GACGTACTCTCA 3'

PgsA 25-70 a.a fragment sequence (PgsA7)
SEQ ID NO 33:
5'CACGTATTTATTGCCATTCCGATCGTTTTTGTCCTTATGTTCGCTTT
CATGTGGGCGGGAAAAGCGGAAACGCCGAAGGTCAAAACGTATTCTGAC
GACGTACTCTCAGCCTCATTTGTAGGCGATATTATGATGGGA 3

PgsA 25-100 a.a fragment sequence (PgsA8)
SEQ ID NO 34:
5'CACGTATTTATTGCCATTCCGATCGTTTTTGTCCTTATGTTCGCTTT
CATGTGGGCGGGAAAAGCGGAAACGCCGAAGGTCAAAACGTATTCTGAC
GACGTACTCTCAGCCTCATTTGTAGGCGATATTATGATGGGACGCTATG
TTGAAAAAGTAACGGAGCAAAAAGGGGCAGACAGTATTTTTCAATATGT
TGAACCGATCTTTAGAGCCTCGGATTATGTAGCA 3'
``` pKV-Pald-PgsA-EGFP was cleaved with EcoRV and BamHI to remove the PgsA gene region and to obtain the vector region.

Figure 11:
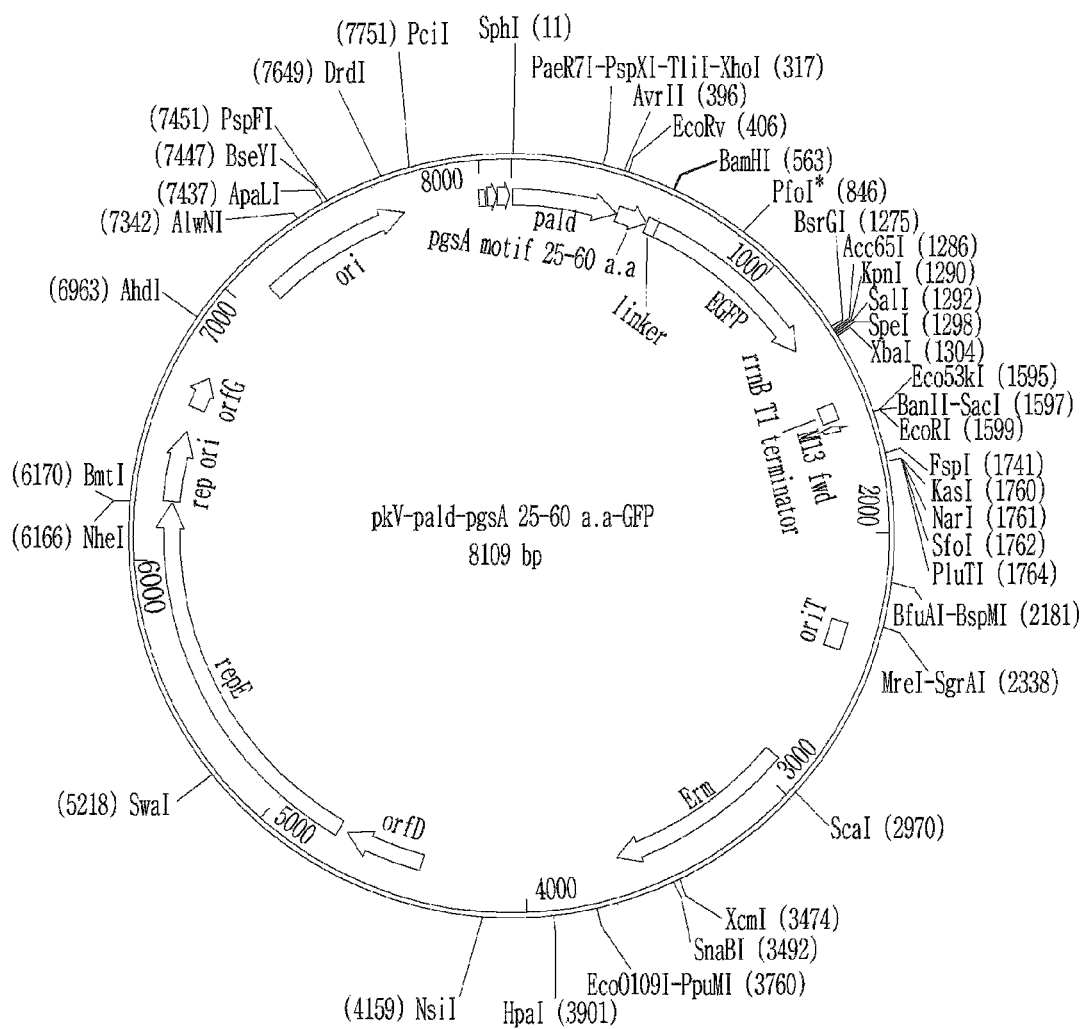
FIG. 11 shows a genetic map of the surface expression vector pKV-Pald-pgsA6 (pgsA motif 25-60 a.a)-EGFP according to the present invention, which uses Lactobacillus casei as a host.
Figure 12:
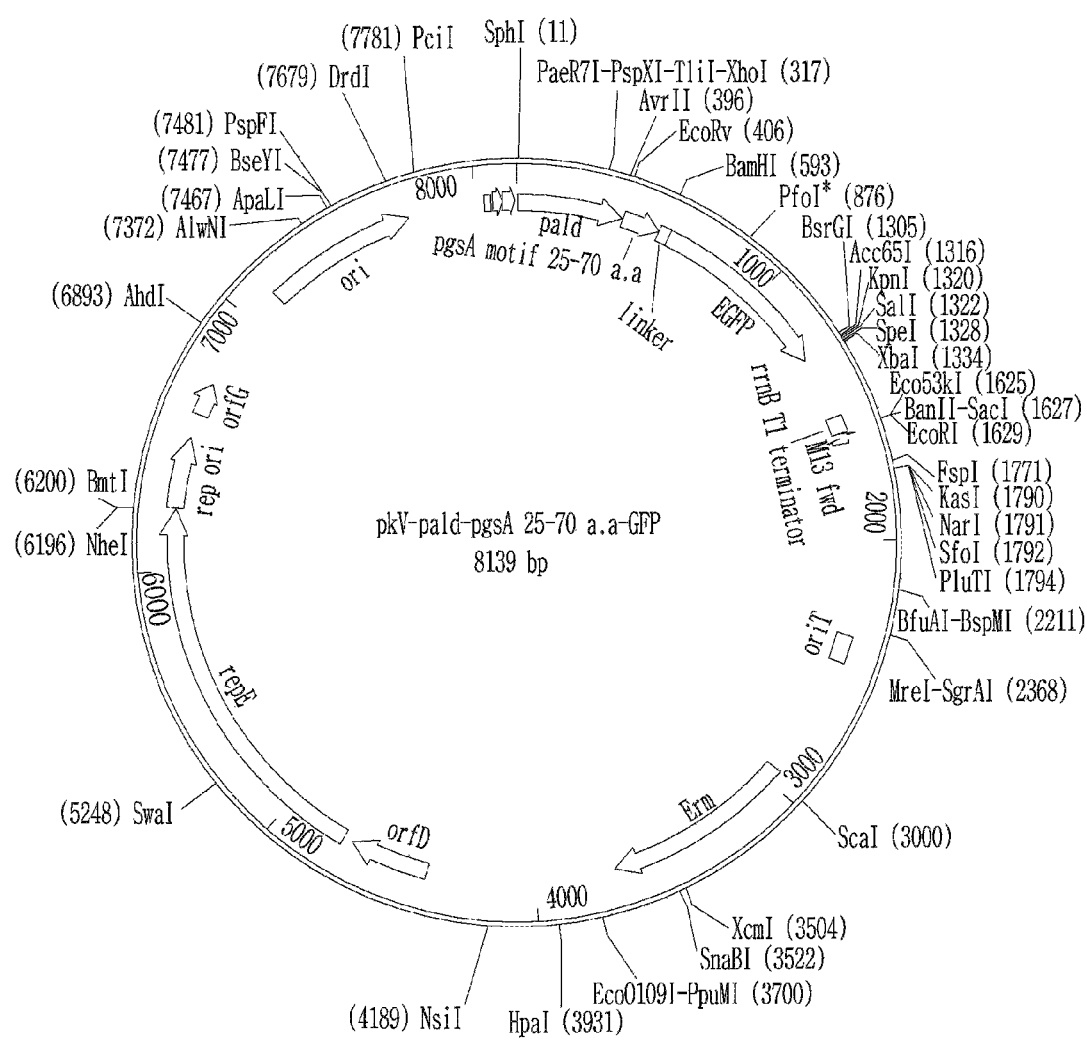
FIG. 12 shows a genetic map of the surface expression vector pKV-Pald-pgsA7 (pgsA motif 25-70 a.a)-EGFP according to the present invention, which uses Lactobacillus casei as a host.
Figure 13:
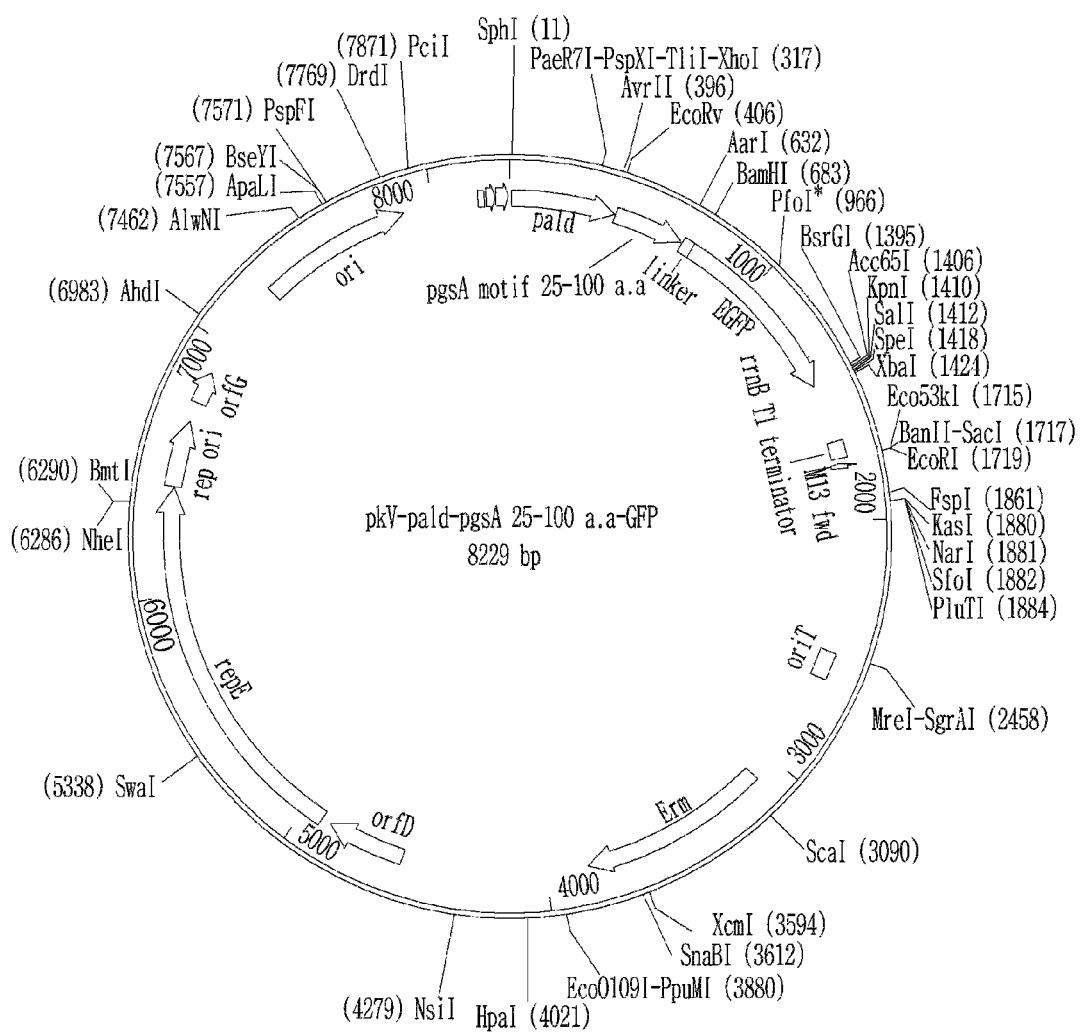
FIG. 13 shows a genetic map of the surface expression vector pKV-Pald-pgsA8 (pgsA motif 25-100 a.a)-EGFP according to the present invention, which uses Lactobacillus casei as a host.

Each of the DNA fragments, cleaved with EcoRV and BamHI and containing the respective PgsA motif fragment genes, was ligated with the vector cleaved with the same restriction enzymes, thus constructing improved vectors (FIGS. 11 to 13).

Example 6: Analysis of Expression on Transformants Obtained by Transformation with PgsA Motif-Improved Surface Expression Vectors In this Example, *Lactobacillus casei* was transformed with each of the PgsA motif-improved surface expression vectors constructed in Example 2, and the transformed recombinant *Lactobacillus casei* was cultured and expression of the EGFP protein thereon was analyzed. Examination was made as to whether the EGFP protein fused with any one of the improved fragments pgsA1 to pgsA8 was expressed on the transformed recombinant *Lactobacillus casei*.

The recombinant *Lactobacillus casei* transformed with each of the surface expression vectors containing each PgsA motif fragment was stationary-cultured in MRS medium (*Lactobacillus* MRS, Becton Dickinson and Company Sparks, USA) at 30° C. to induce surface expression of the EGFP protein fused with the C-terminus of any one of the gene fragments pgsA1 to pgsA8 involved in the synthesis of poly-gamma-glutamate.

Expression of the fusion protein was analyzed by subjecting the cultured *Lactobacillus casei* whole cells to SDS-polyamide gel electrophoresis and to Western blotting using a specific antibody against EGFP.

Specifically, the recombinant *Lactobacillus casei* whole cells on which protein expression was induced were denatured with proteins obtained at the same cell concentration to prepare a sample. The sample was analyzed by SDS-polyacrylamide gel electrophoresis, and then the fractionated proteins were transferred to a PVDF (polyvinylidene-difluoride) membrane (Bio-Rad). The PVDF membrane having the proteins transferred thereto was blocked by shaking in blocking buffer (50 mM Tris-HCl, 5% skim milk, pH 8.0) for 1 hour, and then incubated for 1 hour with a 1:1,000 dilution of an anti-rabbit polyclonal primary antibody against EGFP in blocking buffer. After completion of the incubation, the membrane was washed with buffer and incubated for 1 hour with a 1:10,000 dilution of HRP (horseradish peroxidase)-conjugated anti-rabbit secondary antibody in blocking solution. After completion of the incubation, the membrane was washed with buffer, and the washed membrane was color-developed with a substrate (Lumigen PS-3 acridan, $H_2O_2$) for about 2 minutes. Then, specific binding between the specific antibody against EGFP and the fusion protein was visualized by a CCD camera (FIG. 14).

Figure 14:
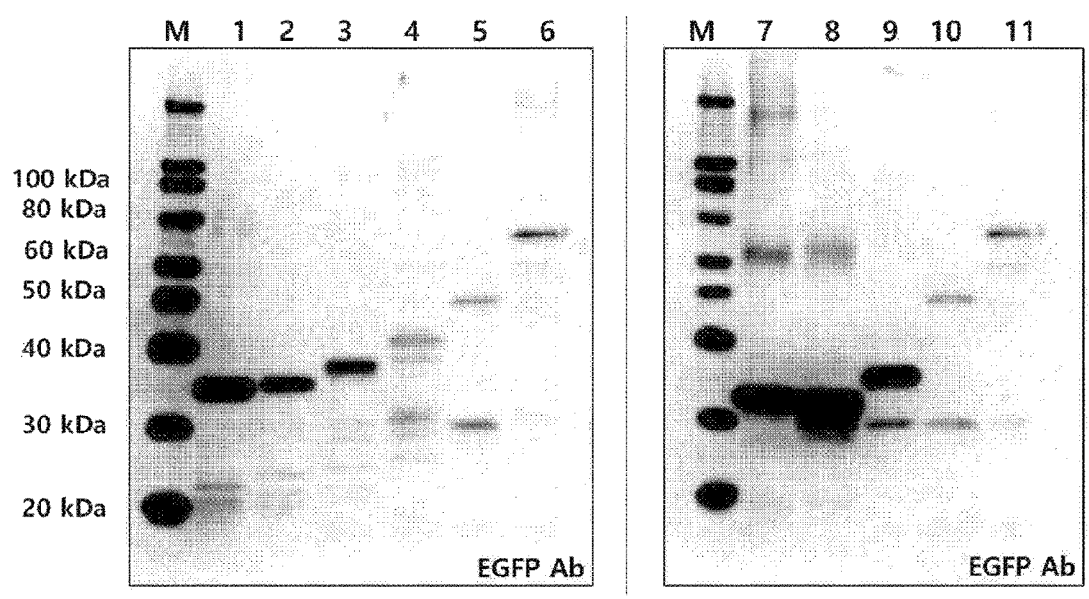
FIG. 14 depicts Western blot images showing the surface expression of EGFP protein in Lactobacillus casei transformed with each of the surface expression vectors pKV-Pald-pgsA1 to pKV-Pald-pgsA8 of the present invention.

FIG. 14 shows expression patterns (lanes 6 and 11) in *Lactobacillus casei* depending on the recombinant expression vector pKV-Pald-pgsA containing the non-improved pgsA as a control for comparison with the present invention, and expression patterns (lanes 1 to 5 and lanes 7 to 10) in *Lactobacillus casei* depending on the recombinant expression vectors pKV-Pald-pgsA1 to pgsA8 containing the improved pgsA1 to pgsA8 according to the present invention.

Specifically, in FIG. 14, lane 1 represents protein expression on the recombinant *Lactobacillus casei* transformed with EGFP fused with PgsA motif 1-60 a.a; lane 2 represents protein expression on the recombinant *Lactobacillus casei* transformed with EGFP fused with PgsA motif 1-70 a.a; lane 3 represents protein expression on the recombinant *Lactobacillus casei* transformed with EGFP fused with PgsA motif 1-80 a.a; and lane 4 represents protein expression on the recombinant *Lactobacillus casei* transformed with EGFP fused with PgsA motif 1-100 a.a. Lane 5 represents protein expression on the recombinant *Lactobacillus casei* transformed with EGFP fused with PgsA motif 1-188 a.a. Lane 6 represents protein expression on the recombinant *Lactobacillus casei* transformed with pKV-Pald-PgsA-EGFP.

In addition, in FIG. 14, lane 7 represents protein expression on the recombinant *Lactobacillus casei* transformed with EGFP fused with PgsA motif 26-50 a.a; lane 8 represents protein expression on the recombinant *Lactobacillus casei* transformed with EGFP fused with PgsA motif 25-70 a.a; and lane 9 represents protein expression on the recombinant *Lactobacillus casei* transformed with EGFP fused with PgsA motif 25-100 a.a. Lane 10 represents protein expression on the recombinant *Lactobacillus casei* transformed with EGFP fused with PgsA motif 1-188 a.a. Lane 11 represents protein expression on the recombinant *Lactobacillus casei* transformed with pKV-Pald-PgsA-EGFP.

It was confirmed that the expression of the EGFP fusion protein comprising the improved PgsA motif fragment was stronger than the expression of the EGFP fusion protein by the non-improved surface expression vector pKV-Pald-pgsA-EGFP.

INDUSTRIAL APPLICABILITY

The present invention relates to a vector which co-expresses two different target proteins on the microbial surface using an aldolase promoter and galactose mutarotase promoter derived from *Lactobacillus casei*, a microorganism transformed with this vector, and a novel vector which effectively expresses a foreign protein on the microbial surface using an outer membrane protein (pgsA) which is derived from a *Bacillus* sp. strain and involved in the synthesis of poly-gamma-glutamate. The surface expression vector according to the present invention is a single vector including: two different promotes; genes encoding a poly-gamma-glutamate synthetase complex for surface anchoring; and target protein-encoding genes linked to the genes encoding the poly-gamma-glutamate synthetase complex, respectively. Thus, the surface expression vector according to the present invention has advantages over prior art inventions in that it may co-express two different target proteins, and the possibility of cellular transformation that may occur in two transformation processes may be minimized because a microorganism transformed with the surface expression vector is used. In addition, since the surface expression vector is a single vector containing two different promoters, it may efficiently express target proteins within a shorter time than conventional art inventions, and has an excellent effect of remarkably reducing drug development costs by selecting substances with high drug potential rapidly and expressing two different target proteins by the single surface expression vector. Therefore, the present invention is industrially applicable.

The invention claimed is:

1. A surface expression vector for expressing target proteins, the surface expression vector comprising: a first promoter, a gene encoding a poly-gamma-glutamate synthetase complex for surface anchoring, and a gene encoding the target protein; and a second promoter, a gene encoding a poly-gamma-glutamate synthetase complex for surface anchoring, and a gene encoding a target protein,
wherein the first promoter is represented by SEQ ID NO: 1,
wherein the second promoter is represented by SEQ ID NO: 2,
wherein the gene encoding the poly-gamma-glutamate synthetase complex is pgsA and has the nucleotide sequence of any one of SEQ ID NOs: 21 to 23 and 32 to 34.

2. The surface expression vector of claim 1, wherein the gene encoding the poly-gamma-glutamate synthetase complex is derived from a *Bacillus* sp. strain.

3. The surface expression vector of claim 1, wherein a linker is inserted into an end of the gene encoding the poly-gamma-glutamate synthetase complex, and the gene encoding the target protein is inserted into the inserted linker.

4. The surface expression vector of claim 1, wherein the first promoter is an aldolase promoter (Pald) derived from lactic acid bacteria.

5. The surface expression vector of claim 1, wherein the second promoter is a galactose mutarotase promoter (Pgm) derived from lactic acid bacteria.

6. The surface expression vector of claim 1, wherein the vector is applied to Gram-negative or Gram-positive bacteria.

7. A microorganism transformed with the surface expression vector of claim 1.

8. The microorganism of claim 7, wherein a microorganism used for the transformation is a microorganism modified so that it does not produce intracellular or extracellular proteases, which are involved in degradation of the expressed target proteins, in order to favor cell surface expression of the target proteins.

9. The microorganism of claim 7, which is lactic acid bacteria.

10. A method for cell surface expression of target proteins, the method comprising steps of: expressing the target proteins on a cell surface by culturing the transformed microorganism of claim 7; and recovering cells having the target proteins expressed on the surface thereof.

11. A method of expressing target proteins on a surface of a Gram-negative or Gram-positive host cell, the method comprising steps of:
(a) constructing a recombinant vector by inserting genes encoding the target proteins into the surface expression vector of claim 6;
(b) transforming the Gram-negative or Gram-positive host cell with the recombinant vector; and
(c) expressing the target proteins on the surface of the transformed host cell by culturing the transformed host cell.

* * * * *

SEQUENCE LISTING

<160> NUMBER OF SEQ ID NOS: 34

<210> SEQ ID NO 1
<211> LENGTH: 406
<212> TYPE: DNA
<213> ORGANISM: Lactobacillus casei

<400> SEQUENCE: 1

```
ccatgcaata cccacttatt gcgatttgct tttctattag ttagcatttt aaattgtgaa      60
acgtgccact tataaacaaa tttccgtctt ctttttatga gagtaatctc atttaatctt     120
gactaaatat ccgattgcgg tcacacaact accagtttca aacaaatttc aatttgatgg     180
```

```
tcattttttta ttttgtcggc aaaaagtgag caaatcagta gcattttccc tgattacggg    240
gtacattcaa agtgactttg cgtacacaca gacatatgta tgacgggtgt tataaaaagc    300
cgtcacgctg ctcgagtagc tctcatcatt ttctcgccct tttctcccgc aacatatgat    360
aaaatacaac ggttgtgaat tgtttatttc ctaggaggat atctac                   406

<210> SEQ ID NO 2
<211> LENGTH: 607
<212> TYPE: DNA
<213> ORGANISM: Lactobacillus casei

<400> SEQUENCE: 2
aattcagcaa gccgcaatac aatgtttctg ttttgaagct tgaagttcca gttgatcaaa     60
agtttgttga aggctacacc gatgacggcg ttacccctgt ttacagcaag gaagaagccg    120
ctaagtatta caaggaacag tcagatgcaa cggatctccc attcatcttc ctgtccgctg    180
gtgtcaccaa cgaattgttc cttgaagaac tcaagtttgc taagcaagca ggttcagcct    240
ttaatggtgt tctctgtggc cgtgcaactt ggaagccggg tgttaagcca tatgctgctg    300
aaggcgaagc tgctggtaag aagtggctgc agaccgaagg caaggctaac attgatcgtt    360
tgaacaaggt gcttgcagaa actgcaaccc cttggactga caaagttgaa ggttaatctt    420
taaccatagt tgcaagaaag gaccgattat gatgatcggt tcttttttta tgactgcgga    480 catgttttg tgaccactgc aaacatcaaa atgaagttcg aaaaacttgc taacaatcat    540
tacaggtcag tgatccagtg gtagactggt attgaatgcg ttttcgtcta ttaggaggta    600
attcaac                                                             607

<210> SEQ ID NO 3
<211> LENGTH: 31
<212> TYPE: DNA
<213> ORGANISM: Artificial Sequence
<220> FEATURE:
<223> OTHER INFORMATION: Forward primer

<400> SEQUENCE: 3
tggtggatcc gtgagcaagg gcgaggagct g                                   31

<210> SEQ ID NO 4
<211> LENGTH: 47
<212> TYPE: DNA
<213> ORGANISM: Artificial Sequence
<220> FEATURE:
<223> OTHER INFORMATION: Reverse primer

<400> SEQUENCE: 4
tgactctaga actagtgtcg acggtacctt acttgtacag ctcgtcc                  47

<210> SEQ ID NO 5
<211> LENGTH: 30
<212> TYPE: DNA
<213> ORGANISM: Artificial Sequence
<220> FEATURE:
<223> OTHER INFORMATION: Forward primer

<400> SEQUENCE: 5
tacggcatgc ttgaattggt ttcttacgat                                     30

<210> SEQ ID NO 6
<211> LENGTH: 30
<212> TYPE: DNA
```

```
<213> ORGANISM: Artificial Sequence
<220> FEATURE:
<223> OTHER INFORMATION: Reverse primer

<400> SEQUENCE: 6
tacgctcgag gttgaattac ctcctaatag                                            30

<210> SEQ ID NO 7
<211> LENGTH: 29
<212> TYPE: DNA
<213> ORGANISM: Artificial Sequence
<220> FEATURE:
<223> OTHER INFORMATION: Forward primer

<400> SEQUENCE: 7
gcgcgaattc ttgaattggt ttcttacga                                             29

<210> SEQ ID NO 8
<211> LENGTH: 28
<212> TYPE: DNA
<213> ORGANISM: Artificial Sequence
<220> FEATURE:
<223> OTHER INFORMATION: Reverse primer

<400> SEQUENCE: 8
gcgctgcgca ttacttgtac agctcgtc                                              28

<210> SEQ ID NO 9
<211> LENGTH: 31
<212> TYPE: DNA
<213> ORGANISM: Artificial Sequence
<220> FEATURE:
<223> OTHER INFORMATION: PCR primer

<400> SEQUENCE: 9
tggtggatcc gtgagcaagg gcgaggagct g                                          31

<210> SEQ ID NO 10
<211> LENGTH: 47
<212> TYPE: DNA
<213> ORGANISM: Artificial Sequence
<220> FEATURE:
<223> OTHER INFORMATION: PCR primer

<400> SEQUENCE: 10
tgactctaga actagtgtcg acggtacctt acttgtacag ctcgtcc                         47

<210> SEQ ID NO 11
<211> LENGTH: 34
<212> TYPE: DNA
<213> ORGANISM: Artificial Sequence
<220> FEATURE:
<223> OTHER INFORMATION: PCR primer

<400> SEQUENCE: 11
tcgagcatgc aatacccact tattgcgatt tgct                                       34

<210> SEQ ID NO 12
<211> LENGTH: 74
<212> TYPE: DNA
<213> ORGANISM: Artificial Sequence
<220> FEATURE:
<223> OTHER INFORMATION: PCR primer

<400> SEQUENCE: 12
tacgggatcc accagaacca ccagaaccac cagaaccacc agaaccacct gagagtacgt           60
```
cgtcagaata cgtt                                                      74

<210> SEQ ID NO 13
<211> LENGTH: 34
<212> TYPE: DNA
<213> ORGANISM: Artificial Sequence
<220> FEATURE:
<223> OTHER INFORMATION: PCR primer

<400> SEQUENCE: 13
tcgagcatgc aatacccact tattgcgatt tgct                                34

<210> SEQ ID NO 14
<211> LENGTH: 74
<212> TYPE: DNA
<213> ORGANISM: Artificial Sequence
<220> FEATURE:
<223> OTHER INFORMATION: PCR primer

<400> SEQUENCE: 14
tacgggatcc accagaacca ccagaaccac cagaaccacc agaaccacct cccatcataa    60
tatcgcctac aaat                                                      74

<210> SEQ ID NO 15
<211> LENGTH: 34
<212> TYPE: DNA
<213> ORGANISM: Artificial Sequence
<220> FEATURE:
<223> OTHER INFORMATION: PCR primer

<400> SEQUENCE: 15
tcgagcatgc aatacccact tattgcgatt tgct                                34

<210> SEQ ID NO 16
<211> LENGTH: 74
<212> TYPE: DNA
<213> ORGANISM: Artificial Sequence
<220> FEATURE:
<223> OTHER INFORMATION: PCR primer

<400> SEQUENCE: 16
tacgggatcc accagaacca ccagaaccac cagaaccacc agaaccacct ttttgctccg    60
ttactttttc aaca                                                      74

<210> SEQ ID NO 17
<211> LENGTH: 34
<212> TYPE: DNA
<213> ORGANISM: Artificial Sequence
<220> FEATURE:
<223> OTHER INFORMATION: PCR primer

<400> SEQUENCE: 17
tcgagcatgc aatacccact tattgcgatt tgct                                34

<210> SEQ ID NO 18
<211> LENGTH: 74
<212> TYPE: DNA
<213> ORGANISM: Artificial Sequence
<220> FEATURE:
<223> OTHER INFORMATION: PCR primer

<400> SEQUENCE: 18
tacgggatcc accagaacca ccagaaccac cagaaccacc agaaccacct gctacataat    60

```
ccgaggctct aaag                                                         74

<210> SEQ ID NO 19
<211> LENGTH: 34
<212> TYPE: DNA
<213> ORGANISM: Artificial Sequence
<220> FEATURE:
<223> OTHER INFORMATION: PCR primer

<400> SEQUENCE: 19
tcgagcatgc aatacccact tattgcgatt tgct                                   34

<210> SEQ ID NO 20
<211> LENGTH: 74
<212> TYPE: DNA
<213> ORGANISM: Artificial Sequence
<220> FEATURE:
<223> OTHER INFORMATION: PCR primer

<400> SEQUENCE: 20
tacgggatcc accagaacca ccagaaccac cagaaccacc agaaccaccg actttctggt       60
acgaaatttt cttt                                                         74

<210> SEQ ID NO 21
<211> LENGTH: 180
<212> TYPE: DNA
<213> ORGANISM: Artificial Sequence
<220> FEATURE:
<223> OTHER INFORMATION: PgsA1

<400> SEQUENCE: 21
atgaaaaaag aactgagctt tcatgaaaag ctgctaaagc tgacaaaaca gcaaaaaaag       60
aaaaccaata agcacgtatt tattgccatt ccgatcgttt ttgtccttat gttcgctttc      120
atgtgggcgg gaaaagcgga aacgccgaag gtcaaaacgt attctgacga cgtactctca     180

<210> SEQ ID NO 22
<211> LENGTH: 210
<212> TYPE: DNA
<213> ORGANISM: Artificial Sequence
<220> FEATURE:
<223> OTHER INFORMATION: PgsA2

<400> SEQUENCE: 22
atgaaaaaag aactgagctt tcatgaaaag ctgctaaagc tgacaaaaca gcaaaaaaag       60
aaaaccaata agcacgtatt tattgccatt ccgatcgttt ttgtccttat gttcgctttc      120
atgtgggcgg gaaaagcgga aacgccgaag gtcaaaacgt attctgacga cgtactctca     180
gcctcatttg taggcgatat tatgatggga                                       210

<210> SEQ ID NO 23
<211> LENGTH: 240
<212> TYPE: DNA
<213> ORGANISM: Artificial Sequence
<220> FEATURE:
<223> OTHER INFORMATION: PgsA3

<400> SEQUENCE: 23
atgaaaaaag aactgagctt tcatgaaaag ctgctaaagc tgacaaaaca gcaaaaaaag       60
aaaaccaata agcacgtatt tattgccatt ccgatcgttt ttgtccttat gttcgctttc      120
atgtgggcgg gaaaagcgga aacgccgaag gtcaaaacgt attctgacga cgtactctca     180
gcctcatttg taggcgatat tatgatggga cgctatgttg aaaaagtaac ggagcaaaaa     240
```

<210> SEQ ID NO 24
<211> LENGTH: 300
<212> TYPE: DNA
<213> ORGANISM: Artificial Sequence
<220> FEATURE:
<223> OTHER INFORMATION: PgsA4

<400> SEQUENCE: 24

```
atgaaaaaag aactgagctt tcatgaaaag ctgctaaagc tgacaaaaca gcaaaaaaag        60
aaaaccaata agcacgtatt tattgccatt ccgatcgttt ttgtccttat gttcgctttc       120
atgtgggcgg aaaagcgga aacgccgaag gtcaaaacgt attctgacga cgtactctca       180
gcctcatttg taggcgatat tatgatggga cgctatgttg aaaaagtaac ggagcaaaaa       240
ggggcagaca gtatttttca atatgttgaa ccgatcttta gagcctcgga ttatgtagca       300
```

<210> SEQ ID NO 25
<211> LENGTH: 564
<212> TYPE: DNA
<213> ORGANISM: Artificial Sequence
<220> FEATURE:
<223> OTHER INFORMATION: PgsA5

<400> SEQUENCE: 25

```
atgaaaaaag aactgagctt tcatgaaaag ctgctaaagc tgacaaaaca gcaaaaaaag        60
aaaaccaata agcacgtatt tattgccatt ccgatcgttt ttgtccttat gttcgctttc       120
atgtgggcgg aaaagcgga aacgccgaag gtcaaaacgt attctgacga cgtactctca       180
gcctcatttg taggcgatat tatgatggga cgctatgttg aaaaagtaac ggagcaaaaa       240
ggggcagaca gtatttttca atatgttgaa ccgatcttta gagcctcgga ttatgtagca       300
ggaaactttg aaaacccggt aacctatcaa aagaattata acaagcaga taaagagatt       360 catctgcaga cgaataagga atcagtgaaa gtcttgaagg atatgaattt cacggttctc       420
aacagcgcca acaaccacgc aatggattac ggcgttcagg gcatgaaaga tacgcttgga       480
gaatttgcga agcaaaacct tgatatcgtt ggagcgggat acagcttaag tgatgcgaaa       540
aagaaaattt cgtaccagaa agtc                                              564
```

<210> SEQ ID NO 26
<211> LENGTH: 38
<212> TYPE: DNA
<213> ORGANISM: Artificial Sequence
<220> FEATURE:
<223> OTHER INFORMATION: PCR primer

<400> SEQUENCE: 26

```
cgctggatat ctacatgcac gtatttattg ccattccg                                38
```

<210> SEQ ID NO 27
<211> LENGTH: 74
<212> TYPE: DNA
<213> ORGANISM: Artificial Sequence
<220> FEATURE:
<223> OTHER INFORMATION: PCR primer

<400> SEQUENCE: 27

```
tacgggatcc accagaacca ccagaaccac cagaaccacc agaaccacct gagagtacgt        60
cgtcagaata cgtt                                                          74
```

<210> SEQ ID NO 28

```
<211> LENGTH: 38
<212> TYPE: DNA
<213> ORGANISM: Artificial Sequence
<220> FEATURE:
<223> OTHER INFORMATION: PCR primer

<400> SEQUENCE: 28
cgctggatat ctacatgcac gtatttattg ccattccg                          38

<210> SEQ ID NO 29
<211> LENGTH: 74
<212> TYPE: DNA
<213> ORGANISM: Artificial Sequence
<220> FEATURE:
<223> OTHER INFORMATION: PCR primer

<400> SEQUENCE: 29
tacgggatcc accagaacca ccagaaccac cagaaccacc agaaccacct cccatcataa   60
tatcgcctac aaat                                                    74

<210> SEQ ID NO 30
<211> LENGTH: 38
<212> TYPE: DNA
<213> ORGANISM: Artificial Sequence
<220> FEATURE:
<223> OTHER INFORMATION: PCR primer

<400> SEQUENCE: 30
cgctggatat ctacatgcac gtatttattg ccattccg                          38

<210> SEQ ID NO 31
<211> LENGTH: 74
<212> TYPE: DNA
<213> ORGANISM: Artificial Sequence
<220> FEATURE:
<223> OTHER INFORMATION: PCR primer

<400> SEQUENCE: 31
tacgggatcc accagaacca ccagaaccac cagaaccacc agaaccacct gctacataat   60
ccgaggctct aaag                                                    74

<210> SEQ ID NO 32
<211> LENGTH: 108
<212> TYPE: DNA
<213> ORGANISM: Artificial Sequence
<220> FEATURE:
<223> OTHER INFORMATION: PgsA6

<400> SEQUENCE: 32
cacgtattta ttgccattcc gatcgttttt gtccttatgt tcgctttcat gtgggcggga   60
aaagcggaaa cgccgaaggt caaaacgtat tctgacgacg tactctca              108

<210> SEQ ID NO 33
<211> LENGTH: 138
<212> TYPE: DNA
<213> ORGANISM: Artificial Sequence
<220> FEATURE:
<223> OTHER INFORMATION: PgsA7

<400> SEQUENCE: 33
cacgtattta ttgccattcc gatcgttttt gtccttatgt tcgctttcat gtgggcggga   60
aaagcggaaa cgccgaaggt caaaacgtat tctgacgacg tactctcagc ctcatttgta  120
ggcgatatta tgatggga                                                138
```

```
<210> SEQ ID NO 34
<211> LENGTH: 228
<212> TYPE: DNA
<213> ORGANISM: Artificial Sequence
<220> FEATURE:
<223> OTHER INFORMATION: PgsA8

<400> SEQUENCE: 34
cacgtattta ttgccattcc gatcgttttt gtccttatgt tcgctttcat gtgggcggga        60
aaagcggaaa cgccgaaggt caaaacgtat tctgacgacg tactctcagc ctcatttgta       120
ggcgatatta tgatgggacg ctatgttgaa aaagtaacgg agcaaaaagg ggcagacagt       180
atttttcaat atgttgaacc gatctttaga gcctcggatt atgtagca                   228
```